US012805717B2

(12) United States Patent
Everett et al.

(10) Patent No.: US 12,805,717 B2
(45) Date of Patent: Nov. 24, 2026

(54) MICRO-BENCH OCT DESIGN

(71) Applicants: Carl Zeiss Meditec, Inc., Dublin, CA (US); Carl Zeiss Meditec AG, Jena (DE)

(72) Inventors: Matt Everett, Jena (DE); Tilman Schmoll, Jena (DE)

(73) Assignees: CARL ZEISS MEDITEC, INC., Dublin, CA (US); CARL ZEISS MEDITEC AG, Jena (DE)

(*) Notice: Subject to any disclaimer, the term of this patent is extended or adjusted under 35 U.S.C. 154(b) by 101 days.

(21) Appl. No.: 18/273,168

(22) PCT Filed: Jan. 31, 2022

(86) PCT No.: PCT/EP2022/052220

§ 371 (c)(1),
(2) Date: Jul. 19, 2023

(87) PCT Pub. No.: WO2022/162224

PCT Pub. Date: Aug. 4, 2022

(65) Prior Publication Data

US 2024/0081638 A1 Mar. 14, 2024

Related U.S. Application Data

(60) Provisional application No. 63/230,970, filed on Aug. 9, 2021, provisional application No. 63/144,376, filed on Feb. 1, 2021.

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0008* (2013.01); *A61B 3/0025* (2013.01);
(Continued)

(58) Field of Classification Search
CPC .............. A61B 13/102; A61B 13/0008; A61B 13/0025; A61B 13/0041; A61B 3/113; A61B 13/152; A61B 2560/0406
(Continued)

(56) References Cited

U.S. PATENT DOCUMENTS 7,126,693 B2 * 10/2006 Everett .............. G01B 9/02091 356/497
7,720,526 B1 * 5/2010 Modell .............. G01B 9/02097 356/497
(Continued)

FOREIGN PATENT DOCUMENTS

CN 103370597 10/2013
CN 103491855 1/2014
(Continued)

OTHER PUBLICATIONS

International Searching Authority, International Search Report and Written Opinion dated Jul. 13, 2022 in International Application PCT/EP2022/052220.
(Continued)

*Primary Examiner* — Sharrief I Broome
(74) *Attorney, Agent, or Firm* — SNELL & WILMER L.L.P.

(57) ABSTRACT

An OCT system constructed on a micro optical bench or semiconductor optical bench includes a hermetically sealed micro package housing a light source and first and second interferometers, where a fraction of the light from the light source is directed to the second interferometer to generate a clock to linearize a scan sweep of the OCT system. An exemplary OCT system uses free space optics and omits the use of fiber optics.

29 Claims, 19 Drawing Sheets

(51) Int. Cl.
*A61B 3/113* (2006.01)
*A61B 3/15* (2006.01)

(52) U.S. Cl.
CPC ............ *A61B 3/0041* (2013.01); *A61B 3/113* (2013.01); *A61B 3/152* (2013.01); *A61B* *2560/0406* (2013.01)

(58) Field of Classification Search
USPC .......................................................... 351/205
See application file for complete search history.

(56) References Cited

U.S. PATENT DOCUMENTS

| | | | | |
|---|---|---|---|---|
| 10,488,177 | B2 | 11/2019 | Flanders | |
| 2007/0055117 | A1* | 3/2007 | Alphonse | G01N 21/49 600/310 |
| 2008/0228033 | A1* | 9/2008 | Tumlinson | A61B 1/00096 600/112 |
| 2011/0096291 | A1* | 4/2011 | Buckland | G01B 9/02078 356/479 |
| 2012/0257210 | A1 | 10/2012 | Whitney et al. | |
| 2014/0125987 | A1* | 5/2014 | Flanders | G01B 9/02059 356/479 |
| 2018/0031363 | A1* | 2/2018 | Johnson | G01N 21/4795 |
| 2019/0049232 | A1 | 2/2019 | Vakoc et al. | |
| 2019/0223714 | A1 | 7/2019 | Raymond et al. | |
| 2020/0138948 | A1 | 5/2020 | Huffstetler et al. | |

FOREIGN PATENT DOCUMENTS

| | | |
|---|---|---|
| CN | 103961059 | 8/2014 |
| CN | 105473055 | 4/2016 |
| CN | 105615824 | 6/2016 |
| CN | 107771050 | 3/2018 |
| JP | 2011523460 | 8/2011 |
| JP | 2014502727 | 2/2014 |
| JP | 2017111062 | 6/2017 |
| JP | 2020010889 | 1/2020 |
| WO | 2015189174 | 12/2015 |
| WO | 2022162224 | 8/2022 |

OTHER PUBLICATIONS

Japan Patent Office, Japanese Office Action dated Jun. 2, 2026 in Application No. 2023-546067.

Japanese Patent Office, Japanese Office Action dated Nov. 28, 2025 in Application No. 2023-546067.

Chinese Patent Office, Chinese Office Action dated Apr. 22, 2026 in Application No. 202280012934X.

Chinese Patent Office, Chinese Search Report dated Apr. 22, 2026 in Application No. 202280012934X.

Chinese Intellectual Property Administration, Second Office Action dated Aug. 25, 2026 in Application No. 202280012934.X.

Japan Patent Office; Notice of Allowance dated Sep. 1, 2026 in Application No. 2023-546067.

* cited by examiner

FIG. 15

Layr1: Inner Limiting Membrane (ILM)
Layr2: (Retinal) Nerve Fiber Layer (RNFL or NFL)
Layr3: Ganglion Cell Layer (GCL)
Layr4: Inner Plexiform Layer (IPL)
Layr5: Inner Nuclear Layer (INL)
Layr6: Outer Plexiform Layer (OPL)
Layr7: Outer Nuclear Layer (ONL)
Layr8: Junction between Outer Segments (OS) and Inner Segments (IS)
Layr9: Externa/Outer Limiting Membrane (ELM/OLM)
Layr10: Retinal Pigment Epithelium (RPE)
Layr11: Bruch's Membrane (BM)

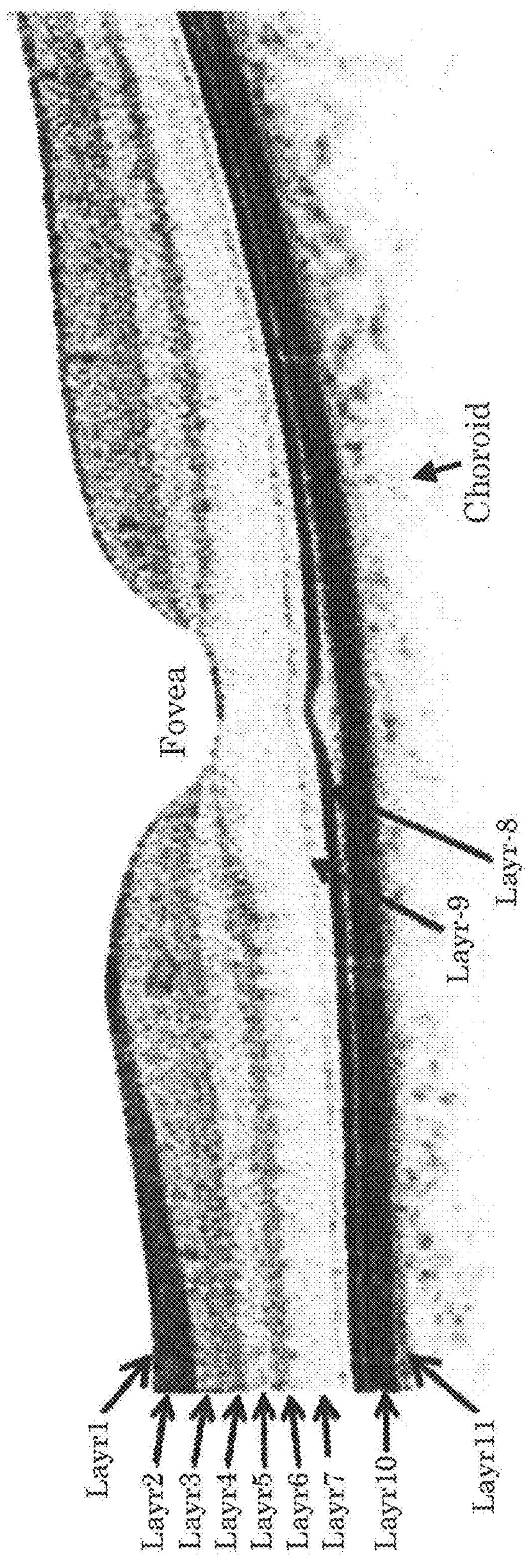

MICRO-BENCH OCT DESIGN

CROSS REFERENCE TO RELATED APPLICATIONS

This application is a U.S. national stage entry under 35 U.S.C. § 371 of International Application No. PCT/EP2022/052220 filed Jan. 31, 2022 entitled "MICRO-BENCH OCT DESIGN", which claims priority to, and the benefit of, U.S. Provisional Application Ser. No. 63/144,376 filed on Feb. 1, 2021, entitled "MICRO-BENCH OCT DESIGN," and claims priority to, and the benefit of, U.S. Provisional Application Ser. No. 63/230,970 filed on Aug. 9, 2021, entitled "MICRO-BENCH OCT DESIGN." Each of the foregoing applications are hereby incorporated by reference in their entirety for all purposes.

FIELD OF INVENTION

The present invention is generally directed to the field of optical coherence tomography (OCT) and Optical Coherence Domain Reflectometry (OCDR) systems. More specifically, it is directed to the use of micro-optics in the design/construction of low cost and/or compact OCT and OCDR systems.

BACKGROUND

There is a great need for compact, low cost Optical Coherence Tomography (OCT) and Optical Coherence Domain Reflectometry (OCDR) systems. An OCDR system measures optical scattering/reflectivity in a sample axially along an optical sampling beam, while an OCT system combines multiple such measurements along a direction orthogonal to the axial illumination to generate a cross-sectional image, or tomogram, of the sample. Typically, the sample is biological tissue, but may be other types of materials.

So far, there have been two primary approaches to achieving lower cost systems; redesign of classic "macroscopic" OCDR/OCT systems (e.g., bulk optic systems using discrete bulk optics and/or fiber optics) to reduce size and cost, and research into implementation of OCDR/OCT systems in semiconductor chips, so-called, "OCT-on-a-chip". Redesign of the macroscopic OCDR/OCT systems, which generally consist of a set of components connected by fiber optics (e.g., light sources, splitters, etc.), has heretofore been unable to achieve the desired cost reduction goals because of the cost of the individual components and overall manufacturing cost of the system. "OCT-on-a-chip" systems, while having the potential to achieve the size and cost reduction goals, have prohibitively expensive non-recurring expenses (NRE), e.g., high initial investment costs, such as research and development into photonic integrated circuit (PIC) design and manufacturing, and investments into development and construction of large scale semiconductor chip (e.g., PIC) manufacturing facilities.

An alternative to photonic integrated circuits is the use of, so-called, micro optical benches or semiconductor optical benches. In a manner similar to a typical optical bench (or optical table or optical breadboard), which may be a straight rigid bar or base (typically marked with a scale) to which lenses, light sources, and other optical components can be attached, a micro optical bench is a substrate base (such as a ceramic bench or other base material) on which locations (e.g., cavities or pits) for receiving, or attaching, micro-optics are constructed.

The potential of micro optical benches in the construction of optical systems has been recognized. For example, light sources (e.g., swept source light sources) have been implemented on micro optical benches, and these light sources have been used in the construction of macroscopic (e.g., bulk-optic based) swept source OCT systems. In addition to providing swept source illumination light, micro optical benches have also been used to implement a k-clock interferometer which interferes a swept source light with itself with a small optical delay to generate a modulated signal that can be used either to trigger an OCT detection system, or to correct for non-linearities in the sweep rate of the swept source. An example of this implementation is described in Bart Johnson, Walid Atia, Seungbum Woo, Carlos Melendez, Mark Kuznetsov, Tim Ford, Nate Kemp, Joey Jabbour, Ed Mallon, Peter Whitney, "Tunable 1060 nm VCSEL co-packaged with pump and SOA for OCT and LiDAR," Proc. SPIE 10867, Optical Coherence Tomography and Coherence Domain Optical Methods in Biomedicine XXIII, 1086706 (22 Feb. 2019); doi: 10.1117/12.2510395.

Semiconductor optical benches are constructed/grown on PIC-style substrates (e.g., single crystal silicon, or other semiconductor wafer). In addition to having openings on a surface (e.g., cavities or pits) for receiving discrete components, the semiconductor optical bench and may also include integrated circuits. Semiconductor optical benches have been employed in telecom applications (e.g., as optical transceivers). It is believed that the use of semiconductor optical benches may potentially enable reduced-size and cost-efficient LIDAR modules for autonomous vehicles. Nonetheless, to the best of the inventor's knowledge, semiconductor optical benches have not been used in the field of medical imaging or OCT.

It is an object of the present invention to reduce the cost and size of an OCT/OCDR system.

It is another object of the present invention to simplify the design and construction of an OCT/OCDR system, e.g., to minimize the use of fiber optics and maximize the use of micro-optics.

It is another object of the present invention to provide for parallelization of the OCT and integration of scanning into a compact design.

It is a further object of the present invention to simplify the calibration of OCT/OCDR systems.

SUMMARY OF INVENTION

The above objects are met in an OCT/OCDR system that identifies the advantages of constructing an OCT/OCDR system on a micro optical bench or semiconductor optical bench, and maximizes those advantages. The present invention achieves compact low-cost Optical Coherence Tomography (OCT) and Optical Coherence Domain Reflectometry (OCDR) systems using a micro or semiconductor optical bench. Both the micro optical bench and semiconductor optical bench may be described as a (typically stiff) base supporting and aligning (e.g., discrete) micro-optics, but the semiconductor optical bench is generally smaller than the micro optical bench and may differ in construction materials and manufacturing processes. A micro optical bench is typically a stiff carrier (such as a ceramic bench or other base material) that hosts several micro-optic elements, which are placed and often actively aligned by a robot. Typical lens diameters are in the range of 0.5 mm to 2.5 mm. A common package for housing a micro optical bench is the standard (e.g., 14-pin) butterfly package or a surface mount device (SMD) package (or other micro package/integrated circuit package). A semiconductor optical bench is typically smaller than the micro optical bench and consists of a (e.g., grown) substrate (e.g., a silicon wafer) having recessed openings (e.g., receptacles, cavities, or pits) on a surface, where the recessed openings are designed to receive and hold micro-optics, or other (e.g., discrete) components, at predefined (X, Y, Z) positions and orientations. This may eliminate (or reduce) the need for active alignment of the received components. Optionally in accord with the present invention, the semiconductor optical bench may also have integrated circuits (ICs) and/or photonic integrated optics, PICs, (e.g., integrated optical circuits) constructed/grown/built into/onto the semiconductor optical bench. Although the present application uses the term micro optical bench (or micro-bench) for the slightly larger, typically stiff-based and/or relaxed-alignment variant, as described above, to differentiate from the semiconductor optical bench, it is acknowledged that semiconductor optical benches have in the prior art sometimes been called micro-optic benches, as well.

Implementation of an OCT/OCDR on either a micro optical bench or semiconductor optical bench can replace the bulk optics and fiber optics of conventional, bulk optic (e.g., macroscopic) systems with micro-optics, greatly reducing cost. The semiconductor optical bench approach also eliminates the need for active alignment, much like the "OCT-on-a-chip" approach discussed above, and thus should be able to achieve costs similar to those expected of "OCT-on-a-chip". Although the semiconductor optical bench concept may require more non-recurring expenses (NRE) than the micro optical bench approach, both approaches could be achieved with lower development effort from the current state of technology than the "OCT-on-a-chip" concepts, while still achieving greater cost reductions and reliability improvements as compared to the redesign of "macroscopic" OCDR/OCT systems. The micro optical bench approach also provides greater flexibility in the integration of components as the components do not need to be constructed from the chip material.

Some features/innovations of the present invention include implementation of an OCDR/OCT system on a micro optical bench or semiconductor optical bench with micro-components (e.g., micro-optics), and/or elimination of fiber optics. Bulk optic components (such as used for "macroscopic" or "bulk optic" OCDR/OCT systems) are expensive, and have additional significant costs associated with addressing issues of alignment between components. Fiber optics, while addressing many of the alignment challenges in bulk optic systems, reduce the stability of the system by adding temperature dependent and motion sensitive polarization effects, with variability in the fiber lengths complicating the design and manufacturing processes. The present approach (particularly using a semiconductor optical bench) permits the creation of reliable free space optics OCT/OCDR systems with minimal alignment/calibration issues.

Other objects and attainments together with a fuller understanding of the invention will become apparent and appreciated by referring to the following description and claims taken in conjunction with the accompanying drawings.

Several publications may be cited or referred to herein to facilitate the understanding of the present invention. All publications cited or referred to herein, are hereby incorporated herein in their entirety by reference.

The embodiments disclosed herein are only examples, and the scope of this disclosure is not limited to them. Any embodiment feature mentioned in one claim category, e.g. system, can be claimed in another claim category, e.g. method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIG. 15 shows an exemplary OCT B-scan image of a normal retina of a human eye, and illustratively identifies various canonical retinal layers and boundaries.

DESCRIPTION OF THE PREFERRED EMBODIMENTS

An OCDR system measures optical scattering/reflectivity in a sample axially along an optical sampling beam, while an OCT system combines multiple such measurements along a direction orthogonal to the axial illumination to generate a cross-sectional image, or tomogram, of the sample. OCT angiography (OCTA) is an extension of OCT, and it identifies (e.g., renders in image format) blood flow in a tissue layer. OCTA may identify blood flow by identifying differences over time (e.g., contrast differences) in multiple OCT images of the same retinal region, and designating differences that meet predefined criteria as blood flow. Since OCDR, OCT, and OCTA are similar in construction and share many components, the present discussion focusses on OCT with the understanding that a person versed in the art would be able to apply the present discussion to OCDR and OCTA. It is to be understood that the present invention applies similarly to OCDR and OCTA, unless otherwise stated.

Generally, optical coherence tomography (OCT) uses low-coherence light to produce two-dimensional (2D) and three-dimensional (3D) internal views of biological tissue, or other sample. Examples of OCT systems are provided in U.S. Pat. Nos. 6,741,359 and 9,706,915, which are herein incorporated in their entirety by reference.

Figure 1A:
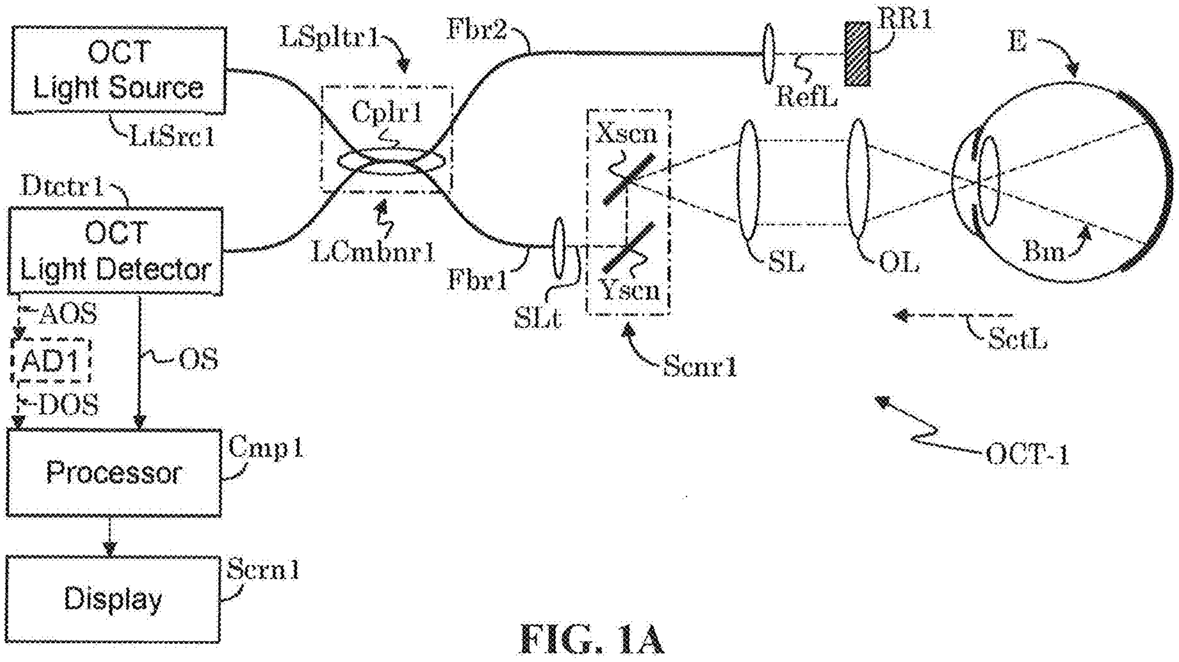
FIG. 1A illustrates a generalized frequency domain optical coherence tomography (FD-OCT) system.

FIG. 1A illustrates a generalized frequency domain optical coherence tomography (FD-OCT) system OCT-1 used to collect 3D image data of an eye E suitable for use with the present invention. FD-OCT system OCT-1 includes a light source, LtSrc1. Typical light sources include, but are not limited to, broadband light sources with short temporal coherence lengths or swept laser sources. Sample light (SLt) from light source LtSrc1 is routed, typically by optical fiber (Fbr1) down a sample arm to illuminate a sample, e.g., eye E; a typical sample being tissues in the human eye. The light source LtSrc1 may, for example, be a broadband light source with short temporal coherence length in the case of spectral domain OCT (SD-OCT) or a wavelength tunable laser source in the case of swept source OCT (SS-OCT). The sample light may be scanned, typically with a scanner Scnr1 between the output of the optical fiber Fbr1 and the sample E, so that the beam of light (dashed line Bm) is scanned laterally over the region of the sample to be imaged. The light beam from scanner Scnr1 may pass through a scan lens SL and an ophthalmic lens OL and be focused onto the sample E being imaged. The scan lens SL may receive the beam of sample light SLt from the scanner Scnr1 at multiple incident angles and produce substantially collimated light, and ophthalmic lens OL may then focus the collimated light onto the sample. The present example illustrates a scan beam Bm that needs to be scanned in two lateral directions (e.g., in X and Y directions on a Cartesian plane) to scan a desired field of view (FOV). An example of this would be a point-field OCT, which uses a point-field beam (beam of light focused to a point) to scan across a sample. Consequently, scanner Scnr1 is illustratively shown to include two sub-scanners: a first sub-scanner Xscn for scanning the point-field beam across the sample in a first direction (e.g., a horizontal X-direction); and a second sub-scanner Yscn for scanning the point-field beam on the sample in traversing second direction (e.g., a vertical Y-direction). If the scan beam were a line-field beam (beam of light focused to a line), e.g., a line-field OCT, which may sample an entire line-portion of the sample at a time, then only one scanner may be needed to scan the line-field beam across the sample to span the desired FOV. If the scan beam were a full-field beam (e.g., a full-field OCT), no scanner may be needed, and the full-field light beam may be applied across the entire, desired FOV at once.

Irrespective of the type of beam used, light scattered from the sample (SctL) is collected. In the present example of FIG. 1A, scattered light SctL returning from the sample is collected into the same optical fiber Fbr1 used to route the light for illumination SLt.

Figure 1B:
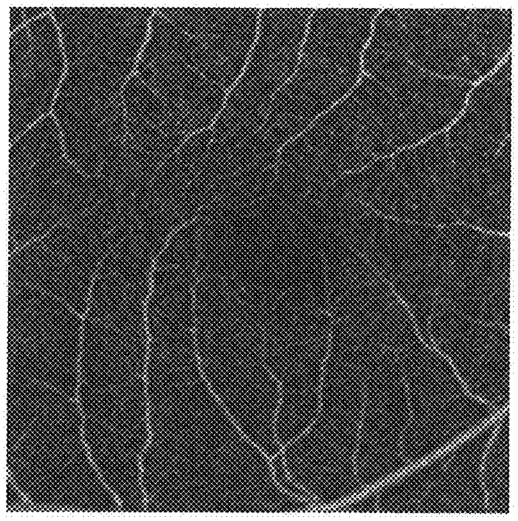
FIG. 1B shows an example of an en face vasculature image.
Figure 1C:
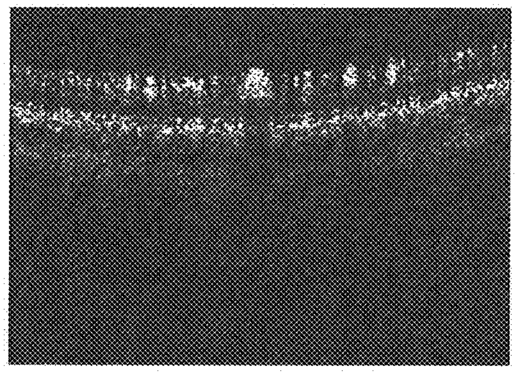
FIG. 1C shows an exemplary B-scan of a vasculature (OCTA) image.

Reference light, RefL, derived from the same light source LtSrc1, travels with the sample light SLt until being split to a separate reference path (e.g., reference arm) by a light splitter LSpltr1, herein implemented as fiber coupler Cplr1. It is to be understood that different types of light splitters are known. The reference path involves optical fiber (Fbr2) and a retroreflector (RR1) with an adjustable optical delay. Those skilled in the art will recognize that a transmissive reference path can also be used and that the adjustable delay could be placed in the sample or reference arm of the interferometer. Collected light scattered from the sample (e.g., scattered light SctL returning from the sample arm) is combined with reference light RefL returning from the reference arm by a light combiner LCmbnr1, herein embodied by fiber coupler Cplr1. Again, it is to be understood that different types of light combining mechanisms are known in the art. The reference light RefL and scattered light SctL then travel together to OCT light detector Dtctr1 (e.g., photodetector array, digital camera, etc.), where interference between the reference light RefL and scattered light SctL generates the OCT signal, OS, which may be passed to an electronic processor Cmp1 (or computer system) that converts the observed interference into depth information of the sample. The depth information may be stored in a memory associated with the processor Cmp1 and/or displayed (e.g., as a scan image such as illustrated in FIGS. 1B and 1C) on a display (e.g., computer/electronic display/screen) Scull. The processing and storing functions may be localized within the OCT instrument, or select functions may be offloaded onto (e.g., performed on) an external processor (e.g., an external computing device at a local or remote site), to which the collected data may be transferred (e.g., wired or wirelessly by, for example, a peer-to-peer connection or via a computer network such as a local area network, wide area network, the Internet, etc.).

In the present example, the interference between reference light RefL and scattered light SctL occurs at the light combiner LCmbnr1 (implemented as fiber coupler Cplr1), but could also occur at an optical component between the light combiner LCmbnr1 and the detector Dtctr1. For example, if the reference light RefL and scattered light SctL had orthogonal polarization states when being combined by the light combiner LCmbnr1, then the interference could be generated by a polarizer (not shown) at forty-five degrees relative to the polarization states of RefL and SctL as described in U.S. Pat. No. 7,126,693B2, herein incorporated in its entirety by reference. For illustration purposes, the system 700*b* of U.S. Pat. No. 7,126,693B2 is herein reproduced as FIG. 1D, and the polarizer is identified as component 752*b*. For purpose of discussion, the component that creates the interference will hereinafter be referred to as an interference generator, IG.

Returning to FIG. 1A, although a single fiber port is shown going to the detector Dtctr1, those skilled in the art will recognize that various designs of interferometers can be used for balanced or unbalanced detection of the interference signal. Optionally, an output analog OCT signal, AOS, from the detector Dtctr1 may be converted to a digital OCT signal, DOS, by an analog-to-digital converter (ADC) AD1 and then supplied to the processor (e.g., internal or external computing device) Cmp1.

Figure 1E:
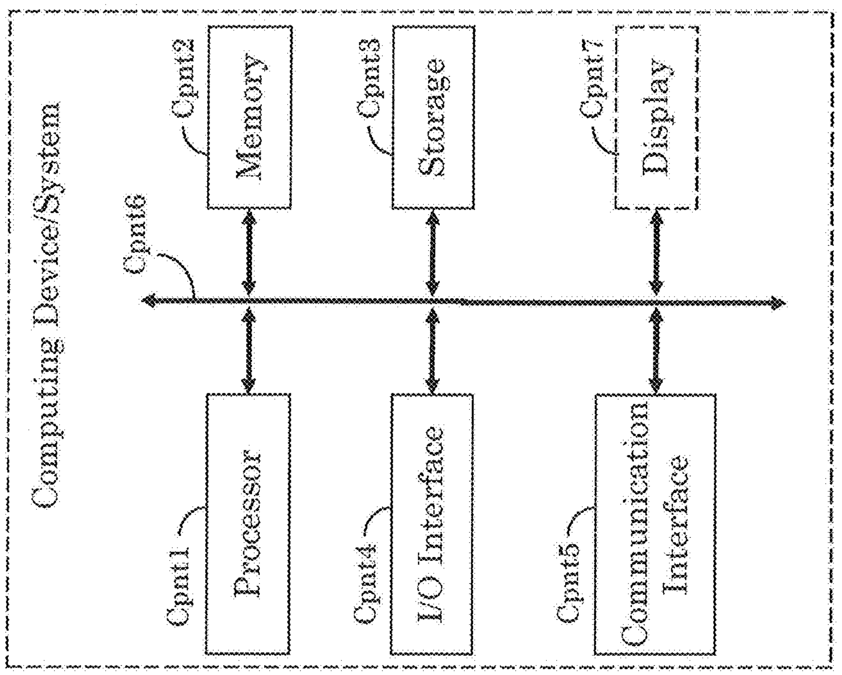
FIG. 1E illustrates an example computer system (or computing device or computer).
Figure 1D:
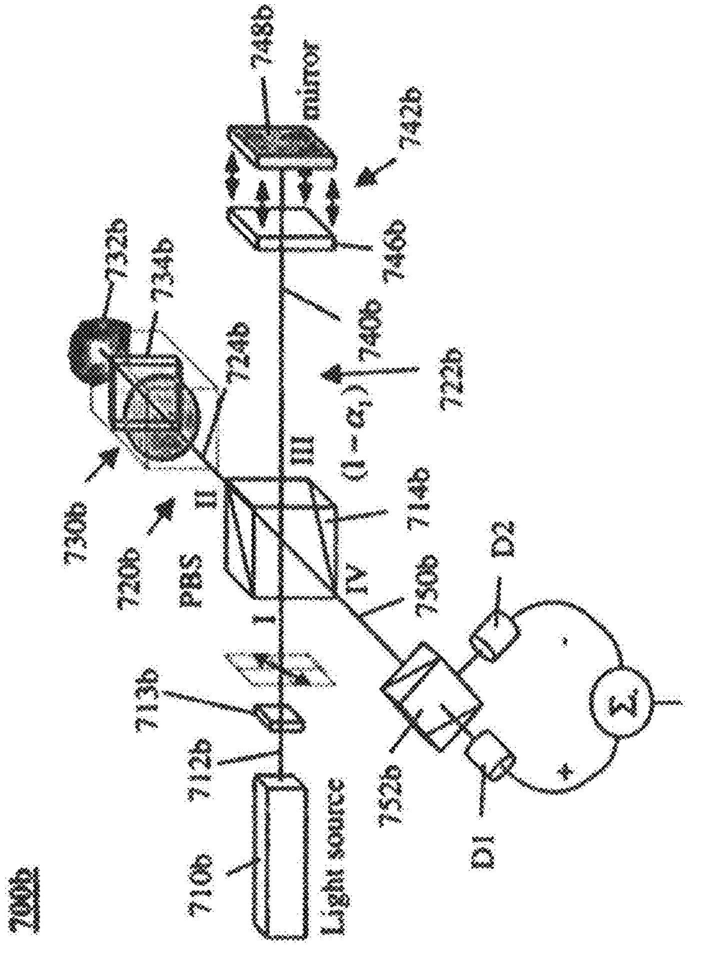
FIG. 1D shows an OCT with orthogonal polarization states using a polarizer to generate interference between light returning from a reference arm and a sample arm.

An example of a computing device (or computer system) is shown in FIG. 1E. This unit could be dedicated to data processing or perform other tasks which are quite general and not dedicated to the OCT device. The processor (computing device) Cmp1 may include, for example, a field-programmable gate array (FPGA), a digital signal processor (DSP), an application specific integrated circuit (ASIC), a graphics processing unit (GPU), a system on chip (SoC), a central processing unit (CPU), a general purpose graphics processing unit (GPGPU), or a combination thereof, that may performs some, or the entire, processing steps in a serial and/or parallelized fashion with one or more host processors and/or one or more external computing devices. A fuller discussion of an exemplary computing device is provided below.

The sample and reference arms in the interferometer could consist of bulk-optics, fiber-optics, or hybrid bulk-optic systems and could have different architectures such as Michelson, Mach-Zehnder or common-path based designs as would be understood by those skilled in the art. Light beam as used herein may be any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—Holographic Optical Coherence Tomography," Optics Letters, 36(13): 2390 2011; Y. Nakamura, et al, "High-Speed Three Dimensional Human Retinal Imaging by Line Field Spectral Domain Optical Coherence Tomography," Optics Express, 15(12):7103 2007; Blazkiewicz et al, "Signal-To-Noise Ratio Study of Full-Field Fourier-Domain Optical Coherence Tomography," Applied Optics, 44(36):7722 (2005)). In time-domain systems, the reference arm needs to have a tunable optical delay to generate interference. Typically, balanced detection systems are used in TD-OCT and SS-OCT systems, while spectrometers are used at the detection port for SD-OCT systems.

The present invention may be applied to any type of OCT/OCTA/OCDR system, such as those discussed above, but is herein fully or partially constructed onto a micro and/or semiconductor optical bench, or similar device having specially configured/shaped recesses, each designed to receive and hold a specific micro-optic device (or other (e.g., discrete) component) at a pre-specified position, and preferably at a pre-specified elevation and orientation. For ease of discussion, one or more features of the present invention are described as applied to a semiconductor optical bench with the understanding that the same feature(s) may apply to a micro optical bench, unless otherwise stated. Other fiducials common in lithographic processes could also be used for placement of the specific micro-optic devices at pre-specified positions. Various aspects of the invention could apply to any type of OCT/OCTA/OCDR system or other types of ophthalmic diagnostic systems and/or multiple ophthalmic diagnostic systems including but not limited to fundus imaging systems, visual field test devices, and scanning laser polarimeters.

In a SS-OCT system configuration using a light source with a long instantaneous coherence length, a variable delay (e.g., adjustment of the reference arm's optical path length in accordance with the depth/axial position of the sample region to be imaged, as described elsewhere herein) may not be necessary to position the sample within the (system's) depth imaging window. Instead, a large optical path length mismatch between reference and sample light may be tolerated. For example, a large imaging depth may be generated, large enough so that the sample would, in a typical imaging scenario, always be within the depth imaging window. The acquired image could then be cropped to only display a region of interest (e.g., a desired depth range). This region of interest may change dynamically during an acquisition for example to compensate for sample motion. This cropping approach however requires sufficiently fast digitization electronics (e.g., analog-to-digital converters) to resolve the high frequency interference signals corresponding to the maximum imaging depth, which can be difficult to achieve, particularly in a cost-effective manner, using stand-alone video cards, video capture cards, daughter boards, and other discrete components. However, high speed detection and/or digitizing electronics (circuitry) may be achievable by integrating the detection and/or digitizing electronics (circuitry) directly onto the same substrate/base as the semiconductor optical bench (or IC on the same substrate/base as the micro optical bench, e.g., in a manner similar to a system-on-chip, SOP, or integrated circuit board approach) on which the present OCT system is constructed. Higher operating speeds may be achieved at least in part due to the smaller traces (and optionally lower rail-to-rail voltage swings) associate with commonly integrated circuits, which avoid/mitigate the high frequency interference issues between long traces/lead lines/wires and the large capacitive loads, large signal propagation delays, and general timing issues associated with routing traces/lead lines/wires for interconnecting with external, discrete components.

Alternatively, one could downmix (or modulate or down-convert or frequency-mix or frequency-shift) the analog OCT signal with a frequency corresponding to one edge of the desired imaging window (either the minimum or maximum path length mismatch), thus creating a downmixed OCT signal with a spectral content corresponding to that obtained if one had adjusted the reference arm path length to this imaging depth. This downmixing would typically be achieved by frequency mixing of the OCT signal with the downmixing frequency to generate frequencies at the OCT signal plus or minus the downmixing frequency, and then filtering to remove (or select or isolate) the summed (or modulated or mixed or shifted) frequency. One may choose the downmixing frequency such that the zero frequency is slightly outside of the scan range of interest to avoid noise near zero frequency and/or to provide a buffer whereby the downmixing frequency can be adjusted if signal appears in this band near zero frequency; in a standard SS-OCT system, a similar effect may be accomplished by making the reference arm length slightly outside the sample depth range of interest. Downmixing the OCT signal in this manner can provide multiple benefits. Most relevant for the present optical bench (semiconductor optical bench or micro optical bench) designs, downmixing allows a significant mismatch in (optical) path length between the reference arm and sample arm, making it possible to integrate a short reference arm (e.g., shorter than the distance to the sample (e.g., retina) position) on the micro-bench (or semiconductor optical bench), which does not leave the micro package, and making the down mixing frequency adjustable can eliminate the need for mechanical or optical adjustment of the reference or sample arm path length.

To quickly find the appropriate downmixing frequency, one could initially sweep the source slowly to generate a large scan range at a relatively slow A-scan rate, and then once the desired scan depth has been identified, switch to a faster sweep rate and corresponding A-scan rate, with the appropriate downmixing frequency to set the scan depth correctly for the resulting more limited scan range.

Electronic adjustment of the downmixing frequency provides rapid adjustment of the depth (axial position) of the imaging window, making it possible to adjust the scan depth to follow (e.g., the curvature of) the sample (e.g., retina) during an acquisition, even shifting the scan depth to follow the sample between or during A-scans within a B-scan (e.g., adjust the path length during acquisition to follow the overall sample position, the sample surface, or a particular layer in the sample). Various methods could be used for following the surface or layer, where examples include adjusting the downmixing frequency based on the spectrum of the OCT signal, or based on identification of a particular layer or boundary in the OCT image found through signal processing of the OCT. For the case of imaging of the retina, a likely surface to follow would be the RPE, or one could track the retina as a whole. To track the retina as a whole, one might maintain the spectrum acquired by the OCT digitization near the midpoint of the bandwidth range supported by the digitization, while to track the RPE, one might maintain the peak spectral signal, likely corresponding to the RPE, at a fixed frequency.

The down-mixing approach to shifting the scan depth has the benefit of not adding a Doppler shift to the OCT signal, as would be generated by movement of the reference mirror to adjust the scan depth. This Doppler shift is undesirable as it affects the image, causing phase wash-out in SD-OCT systems and a displacement in axial position or an axial point spread function (PSF) broadening in swept source systems. The electronic adjustment of the downmixing frequency could be achieved through the use of a voltage controlled oscillator.

As an alternate to implementing the downmixing electronically, one could also achieve the same effect through shifting of the optical frequency of either the sample or reference light. To create a respective frequency shift, optical modulators, such as acousto-optic modulators or electro-optic modulators, can be used. In a hybrid micro-bench/PIC system, this modulation could be provided in the PIC.

One possible complication of changing the down-mixing frequency during acquisition could occur during angiographic imaging, where two OCT scans taken at slightly different times are compared, with the differences between the scans indicating motion, usually attributed to blood flow. If the down-mixing frequency is adjusted between two such scans, one may need to correct for this down-mixing frequency change prior to calculating the difference between the scans so as not to generate artifacts.

In some embodiments one may choose to use the above described down-mixing concepts to enable a large optical path length mismatch between sample arm and reference arm, but may choose to implement some optical path length adjustment optically for sample alignment in the axial direction. This can still be done inside a micro package and without the need for moving parts. For example, one could implement a scanning delay line using an electro optical deflector in combination with a grating and a mirror.

In a preferred embodiment, the above described OCT system is implemented on a semiconductor optical bench, i.e. a semiconductor into which slots (recesses) for the micro optics are etched and the micro-optics are placed without the need for an active alignment process. Such a system would be especially suitable to be produced in large volumes, as it profits from the scalability of semiconductor manufacturing processes. The slots for the micro-optics can be etched for hundreds or thousands of devices in parallel, by patterning entire semiconductor wafers using lithography. The micro-optics can then be assembled by a robot for an entire wafer at a time, followed by a wafer-level packaging step, where a lid wafer is bonded on top of the base layer creating a hermetic seal. Alternatively, another semiconductor optical bench may be used in place of a lid wafer. This "lid" semiconductor optical bench may be constructed with corresponding/complementary slots (or patterns) configured to receive the portions of the micro-optics that extend above the surface of the opposite, "base" semiconductor optical bench. In this configuration, the micro-optics are sandwiched between two semiconductor optical benches, and held in alignment by the two opposing semiconductor optical benches. The lid wafer does not necessarily have to be made of semiconductor material but could also be made of e.g., glass or ceramics without semiconducting properties. This can be beneficial in cases where an operating wavelength at which typical semiconductor materials, as e.g. silicon, are not transparent. Having at least one of a transparent bench wafer or transparent lid wafer is desirable, because the bench or lid typically serve as window through which light can be coupled out of and/or into the micro package. The hermetically sealed package may contain a vacuum to allow faster movement of elements inside the package, e.g. MEMS elements of vertical cavity surface emitting lasers (VCSEL) or MEMS based beam steering mirrors. Alternatively, it may contain specific gasses that prevent or reduce the degradation of active semiconductor optical materials, e.g., damage due to oxidation at the facets of gain chips.

Because the lithographic patterning of the semiconductor wafer creates slots and/or other alignment fiducials with nanometer precision, semiconductor optical benches are especially beneficial for applications where precise control of optical path lengths is required. These include for example multi-beam OCT systems, where the sample is scanned with multiple beams in parallel and a mismatch in imaging depth between the respective imaging channels is undesirable, or for example, for quadrature detectors, where the to be-detected interference signal is split and acquired with a relative phase shift of 90 degree in order to reconstruct the complex signal.

Figure 2B:
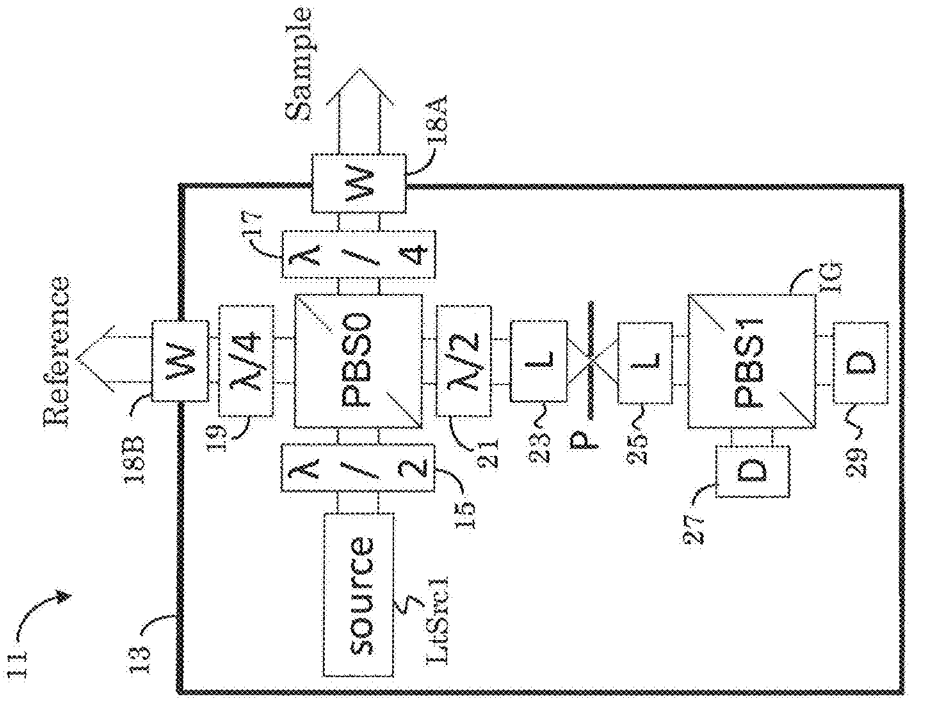
FIG. 2B shows an alternate embodiment of the OCT system of FIG. 2A where windows W (or other transmissive elements) are used as interfaces between the hermetically sealed bench 13 and the outside world, rather than using fiber optics.
Figure 2A:
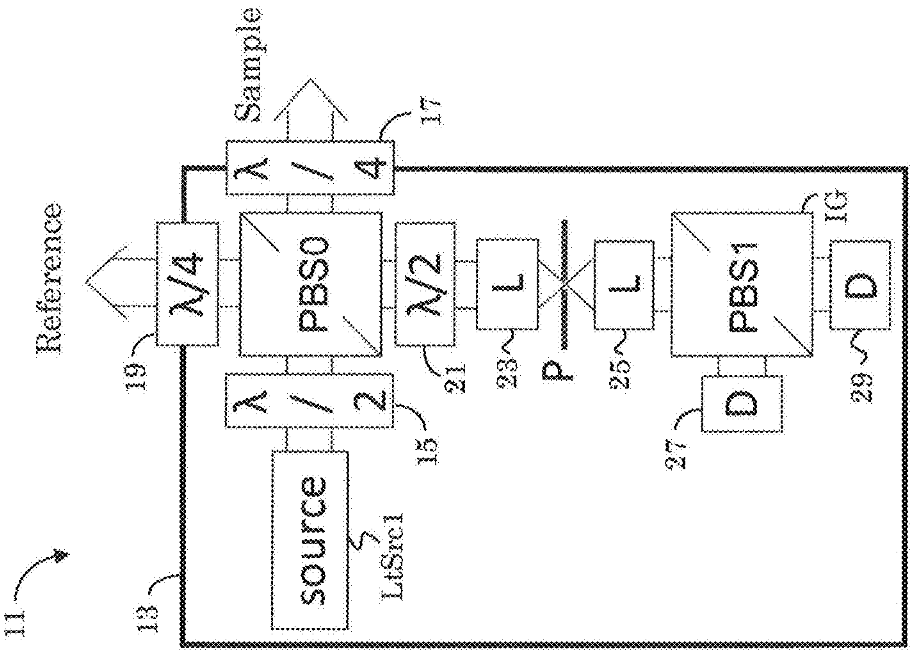
FIG. 2A shows an example OCT system 11 on a semiconductor optical bench 13 (or alternatively on a micro optical bench).

FIG. 2A shows an example OCT system 11 on a base, e.g., a semiconductor optical bench 13 (or alternatively on a micro optical bench). In the present example, light from light source LtSrc1 passes through a half-wave plate (or retarder) 15 (herein symbol lambda λ represents a waveplate, which is an optical device that alters the polarization state of a light wave travelling through it) to a first polarizing beamsplitter (or beam divider) PBS0. The split light then passes through a first quarter-wave plate 17 to go off the bench to a sample (along a sample arm), and passes through a second quarter-wave plate 19 to a reference arm off the bench 13. The returning light from the sample arm (SctL) and from the reference arm (RefL) is combined at first polarizing beamsplitter PBS0 and pass through a second half-wave plate 21, first lens 23 (herein symbol L represents a lens), a (optional) pinhole P, and second lens 25 to reach a second polarizing beamsplitter PBS1, which is preferably at 45 degrees relative to the polarization states of the returning light SctL and RefL and acts as the interference generator IG (e.g., it generates the interferences). The interference signals are then sent to detectors 27 and 29 (herein symbol D represents a detector). The purpose of the various half-wave plates in this description is to change the polarization state such that a portion of the light passes through a polarizing beamsplitter, and a portion of the light is reflected by it. This same function could be performed by waveplate(s) with a different amount of phase delay. For instance, while a half-wave plate at 22.5 degrees could be used to rotate the polarization state by 45 degrees such that half the light is reflected and half transmitted by a polarizing beamsplitter, one could achieve the same 50/50 splitting with a quarter-wave plate rotated at 45 degrees so as to obtain circularly polarized light. One benefit of such an approach could be that all the waveplates could be quarter-wave plates, reducing the number of different components needed. Possibilities for the micro-lenses used in the system include, but are not limited to ball lenses, GRIN lenses, spherical lenses, aspheric lenses, or free-form lenses.

FIG. 2B shows an alternate embodiment of the OCT system of FIG. 2A. Elements similar to those of FIG. 2A have similar reference characters and are described above. In FIG. 2B, windows 18A/18*b* (herein symbol W represents a window), or other transmissive elements, are used as interfaces between the hermetically sealed bench 13 and the outside world, rather than using fiber optics.

Figure 2C:
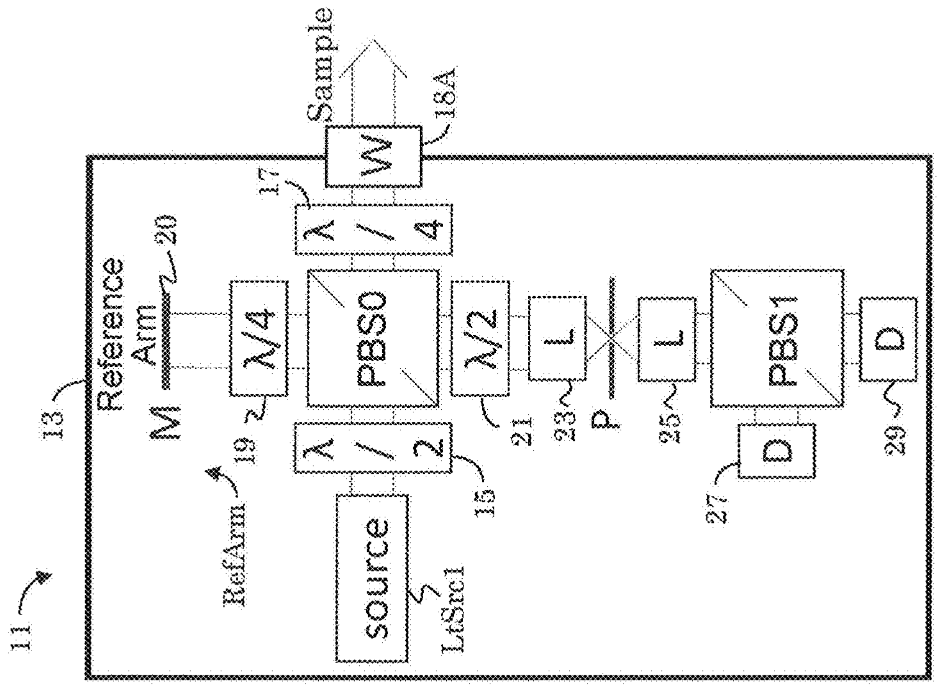
FIG. 2C shows another alternate embodiment where the reference arm RefArm is fully incorporated/integrated on the optical bench 13, eliminating the need for a reference arm interface between the optical bench 13 and the outside world.

FIG. 2C shows another embodiment of an OCT system in accord with the present invention. Elements similar to those of FIGS. 2A and 2B have similar reference characters and are described above. In FIG. 2C, the reference arm RefArm is fully incorporated/integrated on the optical bench 13 (semiconductor optical bench or micro optical bench), eliminating the need for a reference arm interface (e.g., 18B in FIG. 2B) between the optical bench 13 and the outside world. In the present example, a retroreflector (e.g., similar to RR1 of FIG. 1) is implemented as a mirror 20 (herein symbol M represents a mirror). Since one obtains interference when the reference path length matches the sample path length to within the coherence length of the light, several ways that this may be implemented are contemplated herein. One could create a reference arm path length on the optical bench 13 roughly (or substantially) equal in length to the sample arm path length. Alternatively, one could use a light source with a long coherence length in a swept source system and then only make use of a limited scan depth, either by not displaying the complete scan depth, or by down-mixing/demodulating the OCT signal prior to digitization, as discussed above.

Another embodiment may not require external sample arm optics. Instead, the sample could be brought in contact with the micro package or be placed in close proximity to the micro optic package. All sample arm optics would in such an embodiment be part of the micro package. Focusing optics may for example be used to simultaneously serve as the exit/entrance window for the sample beam.

Figure 2D:
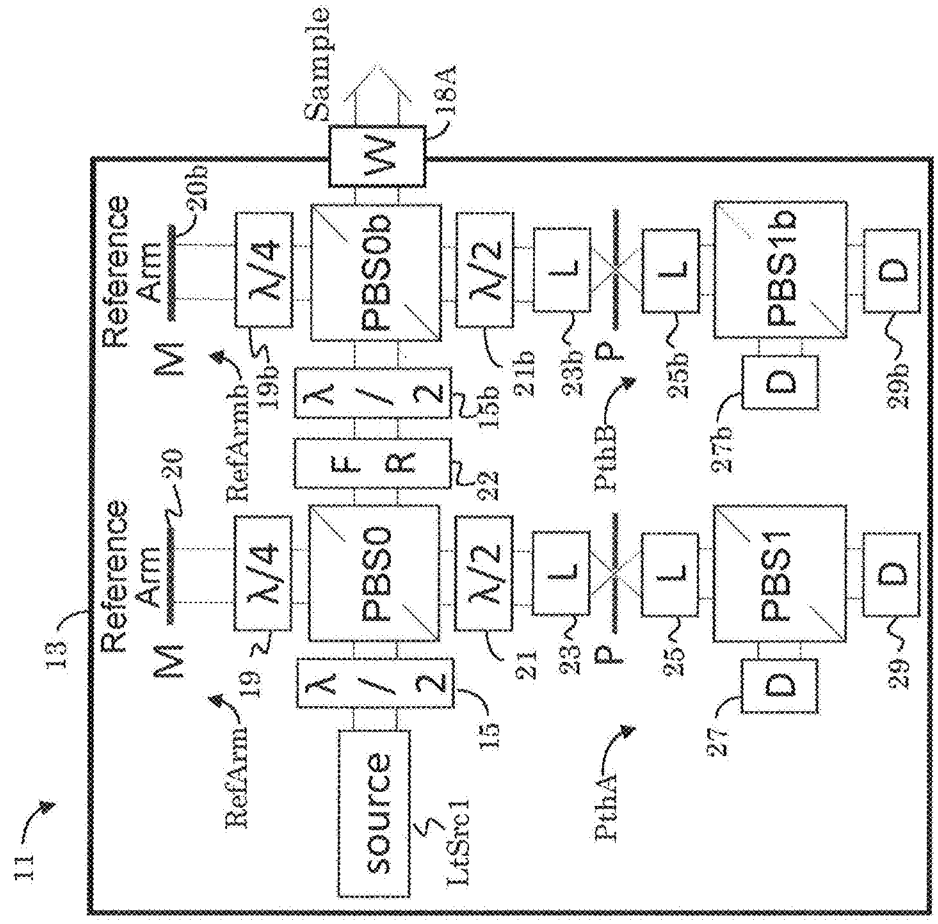
FIG. 2D illustrates an example of a PS-OCT having two detection paths, PthA and PthB, and implemented on a micro optical bench or semiconductor optical bench 13.

Since much of the cost in micro optical bench and/or semiconductor optical bench solutions is in the NRE and packaging, one can increase the complexity of the OCT solution without greatly increasing the overall cost, making more complex designs, such as the polarization sensitive (PS) OCT viable. FIG. 2D illustrates an example of a PS-OCT having two detection paths, PthA and PthB, and implemented on a micro optical bench or semiconductor optical bench 13. Elements similar to those discussed above have similar reference characters, and duplicate instances of similar elements have similar reference characters with the letter “b” appended at their end. In the present example, PBS0 and PBS0*b* deflect light into their corresponding reference arms RefArm and RefArmb, each containing a quarter waveplate 19/19*b* that rotates the polarization state of the light by 90 degrees when double passed, thus causing all the reference light to return through PBS0 and PBS0*b* into the corresponding detector paths PthA and PthB. The two polarization states returning from the sample (e.g., scattered light SctL through window 18A) are separated by PBS0*b*, with the first polarization state passing through polarizer PBS0 to detector path PthA, and the second being reflected by PBS0*b* into detector path PthB. The light returning from the sample to detector path PthA is reflected by PBS0 because its polarization state is rotated by 90 degrees by the combination of the half wave plate 15*b* and faraday rotator 22 (herein symbol FR represents a faraday rotator, which is a type of polarization rotator). This combination half wave plate and faraday rotator also slightly rotates the polarization of the light travelling toward the sample arm, causing some source light to be deflected into reference arm RefArmb. As before, balanced detection is achieved in each of detection path by rotating the polarization state by 45 degrees prior to incidence on the polarizing beam splitters PBS1/PBS1*b* in front of their corresponding detectors 27/29 and 27*b*/29*b*.

Figure 2F:
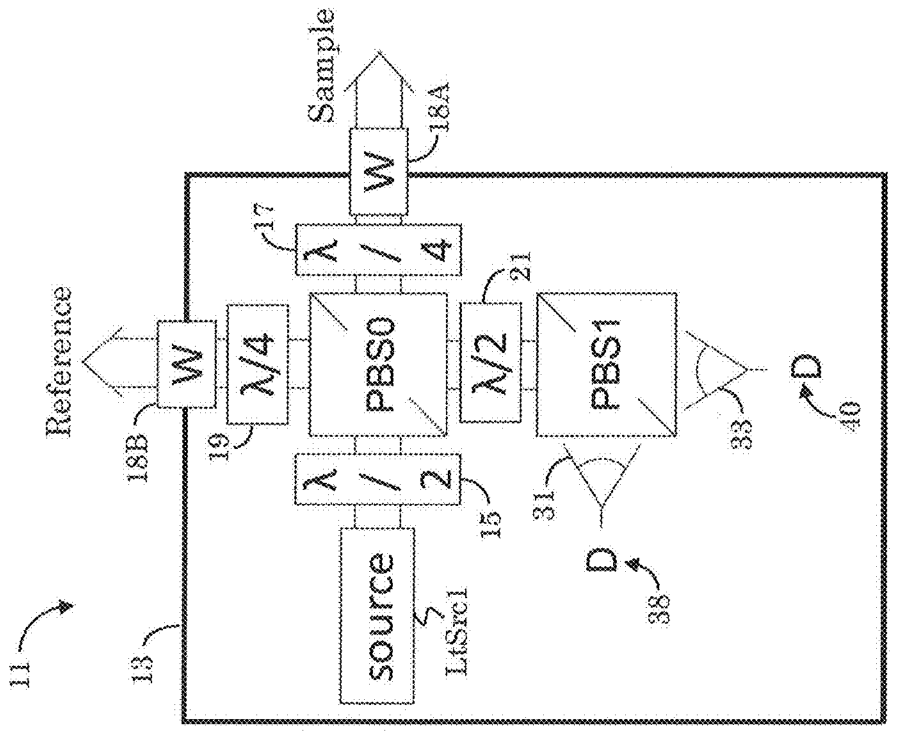
FIG. 2F shows an alternate embodiment of an OCT system that uses windows W to interface between the bench and sample and reference arms, and uses fiber coupling (31 and 33) to interface with detectors 38 and 40.
Figure 2E:
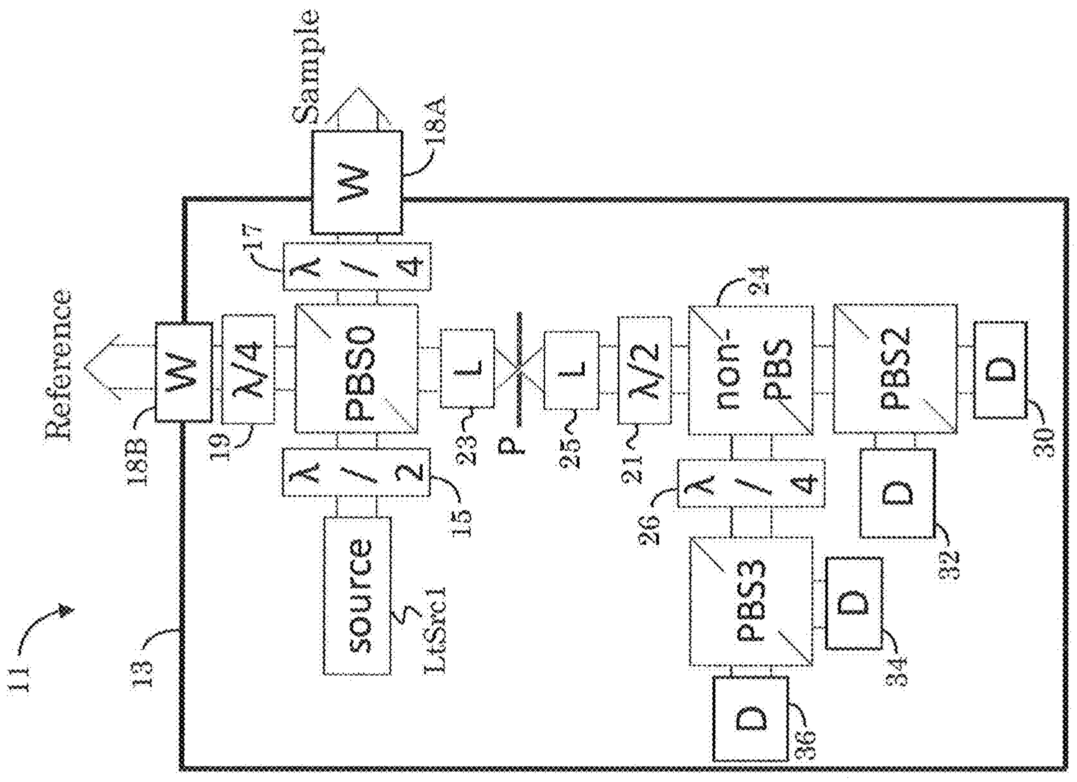
FIG. 2E shows a quadrature detector approach where light in the detection arm (below the pinhole, P) is first split by a non-polarizing beam splitter non-PBS before it travels to two individual polarizing beam splitters PB S2 and PB S3.

FIG. 2E illustrates another approach involving quadrature detection. In this approach, light in the detection arm (below the pinhole, P) passes through half-wave plate 21 and is first split by a non-polarizing beam splitter non-PBS 24 before it travels to two individual polarizing beam splitters PBS2 and PBS3, which reflect their signals to corresponding detectors 30/32 and 34/36. In one of the paths, between non-PBS 24 and PBS3, a quarter waveplate (λ/4) 26 is added to introduce a quarter wave retardance. Quadrature detection enables the system to distinguish between negative and positive differences in path length between the reference arm and the sample, extending the viable scan range across the distance where reference arm path equals the sample arm path by suppressing the complex conjugate mirror image of FD-OCT.

It may also be desirable to integrate other aspects of a clinical OCT system into the micro optical bench or semiconductor optical bench to further miniaturize and cost-reduce the system. Possible examples include:

1) Integrating a second imaging modality such as a scanning laser ophthalmoscope for imaging or tracking of the retina, or both.
2) Providing a fixation target for the eye, possibly using a micro-electromechanical system (MEMS) mirror to direct the fixation target to different locations at the back of the eye to change the patient's fixation location.
3) Focusing and/or aberration correction of the OCT sample to account for differences in the optical properties of different eyes. Such corrections could be done with, for instance, a moving lens within the package, an adjustable mirror (e.g., also within the package), an Alvarez micro-lens, or an electrically tunable lens.

Another benefit of implementing the OCT on a semiconductor optical bench (or micro optical bench) is that the OCT could then be packaged for example in a dual in-line package (DIP) or a surface mount device (SMD) (or other micro package or integrated circuit package) and soldered onto a printed circuit board along with other chips such as the processing electronics for the OCT signal.

Figure 3:
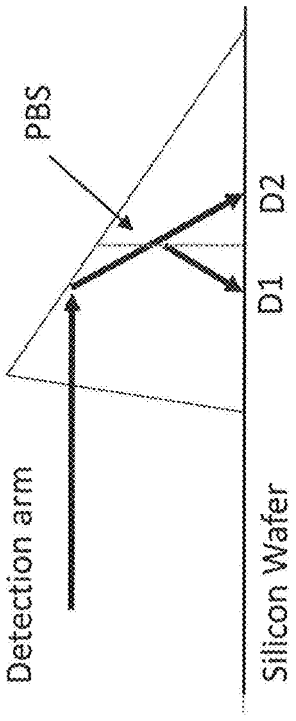
FIG. 3 shows an example of a polarizing beam splitter PBS suitable for receiving light in the detection arm and redirecting it to the silicon wafer surface, and thereby to integrated detectors D1 and D2.

In one or more of the above embodiments, a polarizing beam splitter PBS outputs its respective two beams to corresponding detectors, which may be integrated within (onto) the optical bench 13. FIG. 3 shows an example of a polarizing beam splitter PBS suitable for receiving the light in the detection arm and redirecting it to the silicon wafer surface. In the present example, detectors D1 and D2 are integrated into the semiconductor optical bench.

FIG. 2F shows an alternate embodiment of an OCT system in accord with the present invention. All elements similar to those described above have similar reference characters. Like in the case of FIG. 2B windows W 18A/18B are provided to interface from the bench 13 to sample and reference arms. In the present case, fiber coupling (31 and 33) is used to interface with detectors 38 and 40. However, as mentioned earlier, it is highly desirable to eliminate the fiber optics in the OCT system to improve both stability and manufacturability. The fiber optics in the typical OCT system provide two main benefits: simplification of alignment and spatial mode filtering to ensure single mode interference between the light from the reference and sample arms. The present micro optical bench and semiconductor optical bench technologies address the need for alignment, but do not directly address the need for achieving single mode interferences of the returning signals. To limit the light reaching the detectors to a single mode, or at least sufficiently close to a single mode to achieve good performance from the OCT, the returning light from sample and reference arms may pass through one or more pinholes P (not shown in FIG. 2F) prior to detection, as illustrated in FIGS. 2A through 2E. Also, for simplicity of alignment, and to ensure that both reference and sample light are limited to the same single mode, it is desirable that the sample and reference light pass together through the same pinhole after being combined. Combining the two beams on the same optical path through the use of a polarizing beam splitter rather than having them interfere at the beamsplitter as is done with classic systems provides a shared path for the source and reference light where such a pinhole can be placed as shown in FIGS. 2A through 2E.

Figure 2H:
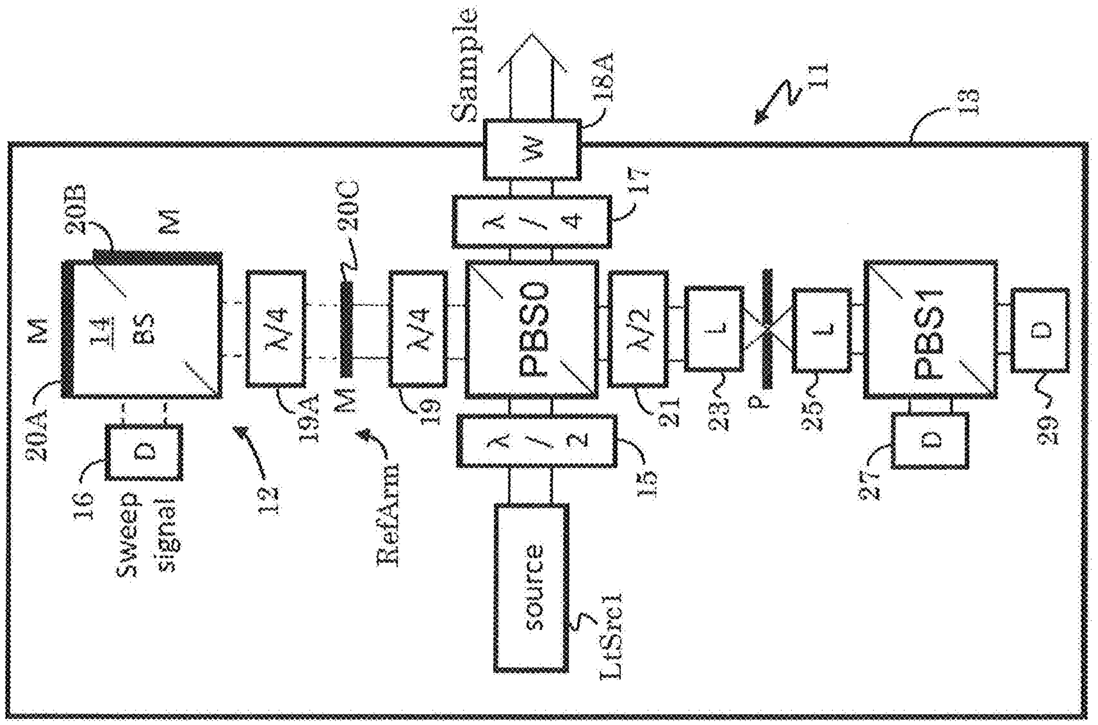
FIGS. 2G and 2H illustrates two embodiments addressing an issue of non-linearity in the frequency sweep of the light source that may be found in swept source OCT systems.
Figure 2G:
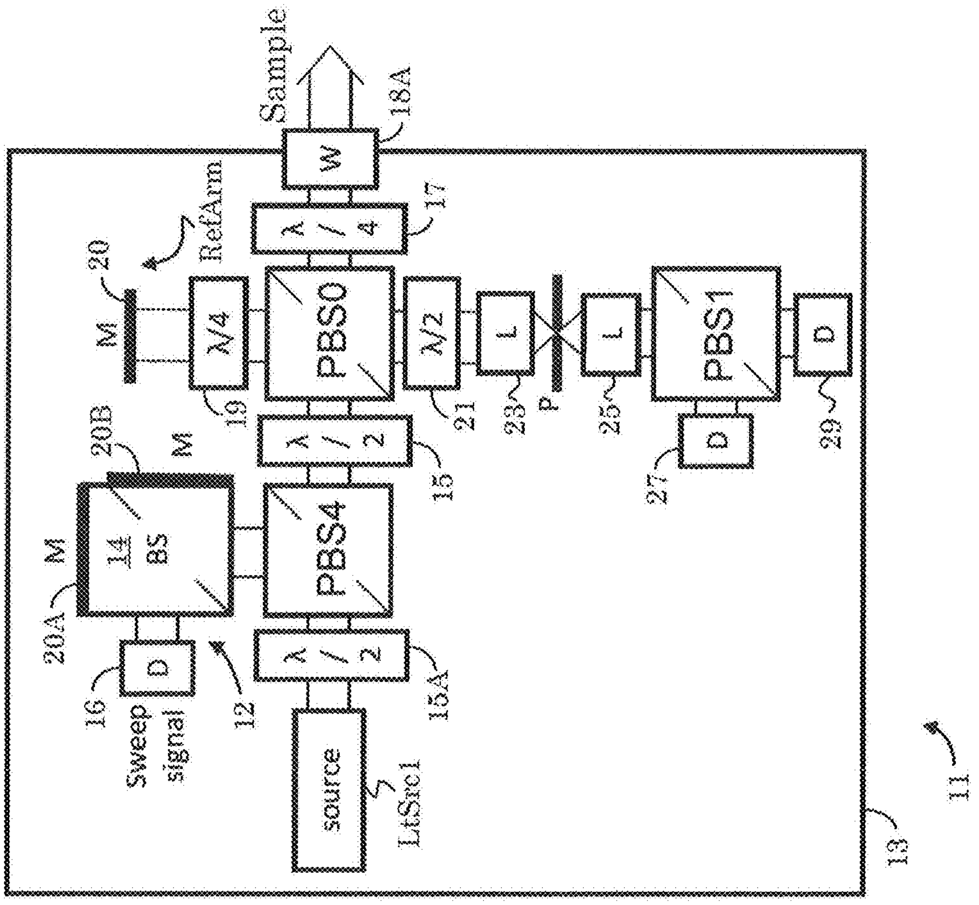

Non-linearity in the frequency sweep of the light source may be an issue in swept source OCT systems. FIGS. 2G and 2H illustrates two embodiments addressing this non-linearity issue. All elements similar to those of FIG. 2C have similar reference characters and are described above. The embodiments of FIGS. 2G and 2H incorporate a second (on-board) interferometer 12, illustratively shown to include a beam splitter 14 (herein symbol "BS" represents a beam splitter), two mirrors 20A and 20B, and a detector 16. By directing a fraction of the light from the source LtSrc1 to the interferometer 12 (e.g., an etalon or Michelson interferometer), one can generate a k-clock for triggering the SS-OCT acquisition, or acquire a reference signal. Either of these configurations can be used for linearizing the sweep (e.g., by means of a sweep signal), where the k-clock trigger directly linearizes the acquisition, and reference signal can be used to determine the nonlinearity and thus correct for it. The light for generating the k-clock or reference signal can be picked off immediately after the source with a PBS and half-wave plate. For example in FIG. 2G, a fraction of light from light source LtScr1 is directed to interferometer 12 by means of half-wave plate 15A and polarizing beam splitter PB S4. Alternatively as illustrated in FIG. 2H, a fraction of light from light source LtScr1 could be directed to interferometer 12 by means of a partially transmissive mirror 20C in the reference arm RefArm (and optionally another quarter-wave plate 19A) followed by the Michelson interferometer 12, which eliminates several components in comparison to the design shown in FIG. 2G.

To avoid additional components for the spatial filtering, the active area of the photodiodes may serve as the spatial filter if their size is chosen accordingly. In this case, one would focus the collection light on to the detectors, and use small detectors, typically less than a few times the size of the focused beam.

The beam out of the micro-optics package may be coupled to additional optics depending on the application (e.g., mirror scanner, beam expander, relay optics to sample). To avoid reflections from these optical surfaces returning to the detectors in the interferometer, the quarter wave plate in the sample path (17 in FIG. 2A) may be placed outside the micro-bench, one option being between the last optic and sample. In this configuration, the reflections from any components in the sample pathway before the quarter wave plate will be directed away from the detectors due to its polarization state.

Reflections from various optical components in the system can lead to detector saturation, VCSEL or optical amplifier damage, and/or artifacts or ghost images in the OCT signal. These undesired reflections can be mitigated or eliminated in various ways including but not limited to: the use of pinholes and apertures, limiting the active area of detectors, gluing components to reduce the refractive index mismatch, anti-reflection coatings, tilted components, and polarization isolation.

The described OCT systems of FIGS. 2A to 2E (and 2G and 2H) can avoid the use of fibers and/or semiconductor waveguides. The absence of fiber avoids signal fluctuations due to changes in birefringence which occur when a fiber is moved or the temperature changes, and the absence of semiconductor waveguides, which typically have sub-micrometer diameters, improves the collection and propagation efficiency as well as alignment stability for example if the probe is dropped or shaken.

In conventional OCT systems, the light in the reference path is reflected back to the interferometer using a corner retroreflector. Corner retroreflectors direct incoming light over a wide range of incident angles, making it ideal for reliably redirecting the reference light in the presence of system tolerances and misalignment. However, corner retroreflectors are expensive and difficult to manufacture at scales less than 1 mm. They can also vary the polarization over the wavefront if the beam is directed at the center of the component. A major advantage of the described micro-optic system is the tight tolerance on optical component mounting, which likely allows use of a planar mirror in place of a retroreflector (20 in FIGS. 2C and 2D). If the system is not capable of ensuring sufficient co-alignment of the sample and reference at the detection with this configuration, the system could instead include a lens with mirror at its back-focal plane (i.e., a cat-eye retroreflector) positioned in the reference path.

As mentioned previously, the described system can be very low cost. The cost of SS-OCT systems is however typically driven by the cost of the tunable light source. It is therefore desirable to use particularly cheap light sources in order to enable an overall low system cost. Vertical cavity surface emitting lasers (VCSEL) are prevalent in many high-volume applications, such as data centers, optical computer mice, distance and proximity sensors, biometric face recognition etc., and are therefore typically very inexpensive. It has previously been shown that it is possible to tune their center wavelength by adjusting their laser drive current. Such a source or a combination of multiple such sources are therefore well-suited to be used in the presently described system. One issue with VCSELs, and particularly thermally driven VCSELs, is the limited wavelength range over which they can be swept. As the axial resolution of the OCT system is determined by the sweep bandwidth of the light, it may be desirable to combine multiple VCSELs with different central wavelengths to achieve an increased combined bandwidth and in some cases increased total optical output power.

Figure 4A:
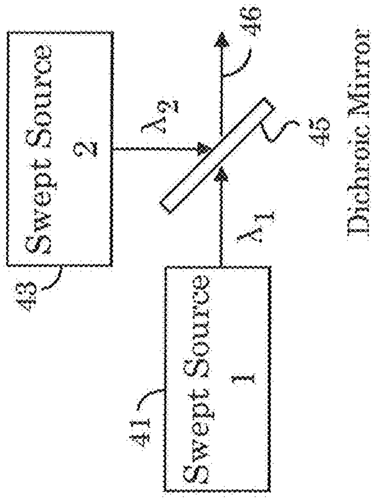
FIG. 4A illustrates one method of combining multiple VCSELs (41/43) using a dichroic mirror 45.

FIG. 4A illustrates one method of combining multiple VCSELs (e.g., swept sources) 41/43 using a dichroic mirror 45. In this approach, the light from swept source 41 passes through dichroic mirror 45 and the light from swept source 43 is reflected by dichroic mirror 45. In this manner both VCSELs 41/43 are combined to define a combined light beam 46.

Figure 4B:
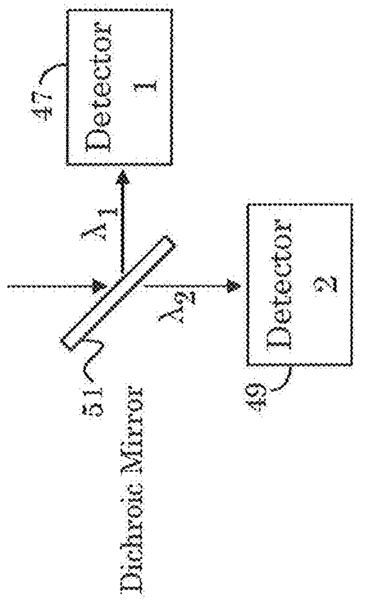
FIG. 4B illustrates the use of another dichromic mirror 51 to split the light at the detection end of the OCT to different detectors (47/49), such as if VCSELs 41/43 of FIG. 4A were operated simultaneously.

With reference to FIG. 4B, if VCSELs 41/43 of FIG. 4A were operated simultaneously, which would be desirable from an optical output power perspective, it would then be desirable to split their light at the detection end of the OCT to different detectors (47/49) through the use of another dichroic mirror 51.

Alternatively, one could operate multiple VCSELs sequentially, and then detect the light from each VCSEL (e.g., two or more VCSELs) on the same detector. Operating the VCSELs sequentially could be beneficial for instance if the VCSELs have a limited duty cycle. The limited duty cycle could be a result of the need for the VCSEL to cool between thermally driven sweeps, or in the case of a MEMS VCSEL, for the MEMS to return to its initial position to start a next sweep.

Figure 5:
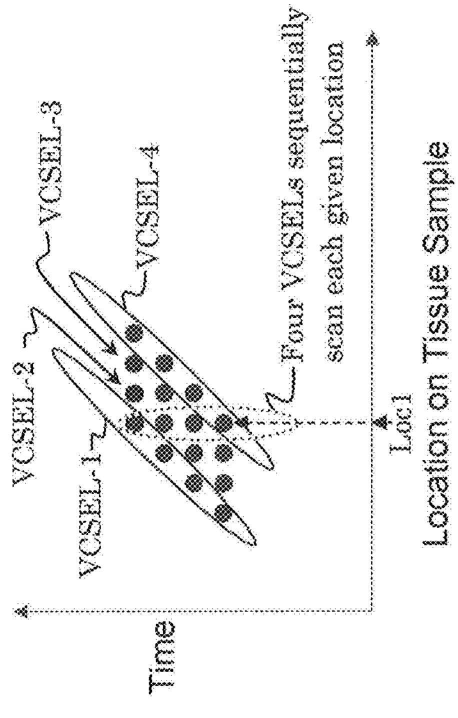
FIG. 5 illustrates an alternate way of scanning a given location in a sample tissue with multiple VCSELs covering different wavelength bands.

FIG. 5 illustrates an alternate way of scanning a given location in the sample tissue with multiple VCSELs covering different wavelength bands. In this example, multiple, different VCSELs (e.g., VCSEL-1, VCSEL-2, VCSEL-3, and VCSEL-4) sequentially illuminate the same location on a (tissue) sample by focusing the different VCSELs along a line and shifting the scan by the distance between the focused VCSELs. FIG. 5 illustrates a plot of Time vs. (illumination) Location on Tissue Sample. In this manner, the same given location on the sample (e.g., location Loc1) is sequentially scanned by the multiple (e.g., four) VCSELs. Optionally, a combination of multiple current-tuned VCSELs may be used. For example, spectrally, one may use more than two VCSELs and sweep pairs/groups with large spectral separation in parallel and then a second set sequentially. The VCSELs may be linearized, and an array of VCSELS may be inserted into a slot in the micro optical bench (or semiconductor optical bench). Alternatively, one or more VCSELs could be integrated into the semiconductor wafer of the semiconductor used in the construction of the optical bench substrate/base, much as the electronics or detectors could be. The use of VCSELs are particularly conducive to this as they emit vertically, directly out of the bench, and thus a simple mirror or turning prism could be used to redirect the VCSEL light along the plane of the semiconductor-based bench.

Another issue with VCSELs is their limited optical output power. For high quality OCT imaging of biological samples they may therefore combined with a semiconductor optical amplifier. However, three aspects specific to the herein described OCT system enable the use of VCSELs for high quality OCT imaging of biological samples without optical amplifiers, which has otherwise not been demonstrated:

1. The high optical efficiency of the free space micro-optics interferometer. Similar optical efficiency is at least in the 800 nm and 1060 nm wavelength range not feasible with fiber based designs, because efficient circulators do not exist at these wavelengths and hence one always loses a lot of power on the path to the sample.
2. The use of low noise detectors instead of p-i-n and transimpedance amplifier based balanced detectors. Because the performance of the herein described system may be significantly limited by the amount of reference light needed to overcome detector noise, it is desirable to use, in contrast to state-of-the-art OCT systems, which are typically not source power starved, very low noise detectors. This enables shot noise limited sensitivity with low reference power. Most of the available optical power can therefore be sent to the sample, by adjusting the waveplate in front of the first polarizing beam splitter accordingly. Suitable low noise detectors for application in the herein described system are electron-injection detectors (E-I detectors). They exhibit low noise, which is due to their inherent amplification less dependent on their RF signal bandwidth.

If only little reference power is required to overcome detector noise as the dominant noise source, relative intensity noise (RIN) of the light source is usually not a concern either. It is therefore possible to omit the balanced detection in such a system and still be shot noise limited. However, because the balanced detection not only suppresses RIN, but also common mode signals, such as auto-correlation signals, it is usually desirable to still use a balanced detection arrangement.

3. The use of VCSEL arrays and hence multiple parallel beams. This will multiply the total optical sample power by the number of VCSEL within the array. Hence, one can achieve equal or higher sample power as state-of-the-art OCT systems using for example a MEMS tunable VCSEL and an optical amplifier. The concept of multiplexing by the use of VCSEL and detector arrays will be described in greater detail at a later section of this document.

Another embodiment may add a partially transmissive element to the sample arm that generates a reflex which then interferes with the reference light. Since the above embodiments already have a number of optical surfaces in the sample arm, one may use a reflex from one of these optic surfaces instead of introducing an additional element. Because this reflex would in any case be closer than the sample, its interference signal would have a lower frequency than the OCT signal. It could therefore be separated from the OCT signal, for example, by splitting the signal and high-pass/low-pass filtering the two copies accordingly. For example, the low frequencies may be used for the reference interference signal and the high frequencies may be used for the OCT signal. The reference interference signal would then be digitized in parallel and used to correct the sweep's wavenumber non-linearity and to phase stabilize the OCT data. Alternatively, reference signal and OCT signal could be digitized together and separated in digital space. This would avoid the need for a second data acquisition channel.

The present invention also envisions other aspects of the OCT system either being implemented on the micro optical bench or semiconductor optical bench, or actually integrated into the semiconductor optical bench. For instance, a MEMS mirror scanning the OCT beam could be either implemented on the bench or integrated into the semiconductor-based bench through photolithography. This MEMS mirror could provide the complete transverse scanning capability for the OCT system, or be one component of the system. In particular, this MEMS mirror could provide rapid scanning over a limited field of view, with the more extended field of view provided by a secondary scanning system. Limiting the field of view of the MEMS scanning system integrated on the micro optical bench and/or semiconductor optical bench (e.g., to less than the desired/predefined/target full (or more extended) scanning FOV of the system, e.g., a wide field scanning system) has several benefits. First, the angular range of a MEMS mirror is typically on the order of +/−6 degrees, making it difficult to address the full field of view desired for a typical OCT system. In a classic (e.g., bulk optic) OCT system, one could use a relatively large MEMS mirror and image the MEMS to a de-magnified spot to increase the field of view, but this is more difficult with the limited space within a DIP (or other typical semiconductor package) for both the mirror and the OCT system. In addition, by limiting the size of the MEMS mirror, one can increase the speed of the scanning, but at the price of not being able to further de-magnify the beam to increase the field of view. Note that the scanning speed of the MEMS mirror could also be increased further through resonant scanning about one axis of scanning. Finally, the resulting scan behavior, with rapid scanning of a small region that is moved relatively slowly across the retina, is beneficial. The fact that the region of interest is moving relatively (or comparatively) slowly across the retina makes it possible to maintain optimum performance of the OCT system, adjusting the axial scan depth, focus, and or other aberrations such as astigmatism to match the properties of the retina at a given location.

One challenge in this configuration is relaying the beam from the scanner to the patient's pupil while maintaining large working distance and compact design of the OCT module. Introducing a converging beam onto the MEMS scanner provides flexibility in the design, including the possibility of relaying the scanner with a single lens positioned a distance slightly larger than the focal length of the lens. The vergence of the beam could also be adjusted by translating a lens before the scanner, providing a focusing element to the design. This configuration provides a compact design with minimal components for pupil relay and focusing.

Addressing the need for fast scanning using a mirror integrated on to the micro/semiconductor optical bench also means that the wide field scanning system can scan at a slower rate, providing greater flexibility in its design. Examples of options enabled by the reduced scan speed requirements include mirrors driven by either galvanometers or by electric motors, or actually moving the OCT system including the MEMS mirror across the field of view. The ultra-compact OCT interferometer design enabled by micro optical bench and semiconductor optical bench solutions makes moving the entire OCT interferometer much more feasible, but one could also use this combination of small field of view fast scanning (on a micro bench) plus wide field of view slower scanning in a more classic fiber optic based OCT system, where the OCT sample arm fiber tip, MEMS scanner, and small field of view optics are moved as a group across the full field of view.

If wide field imaging is provided by moving the OCT system or fiber tip, it is desirable for the system to move along a sphere (e.g., spherical surface/plane) centered at the pupil so as to maintain a fixed working distance relative to the pupil. In addition to the benefit of maintaining the working distance, one can design the mechanism for generating the motion on the sphere to have an element that remains parallel to the sphere surface as it moves along the sphere. One can then mount the OCT/optical imaging system to have an optical axis perpendicular to this element parallel to the sphere, thus ensuring that the imaging system remains pointed toward the center of the sphere, where the pupil resides, as the system is scanned across the field of view.

For several reasons, it may be desirable to have the center of the sphere somewhat displaced from the pupil during the scan. Possible reasons include, but are not limited to:

1) Simplifying alignment by allowing flexibility in the pupil location relative to the center of the scan.
2) Displacing the center of the sphere back from the eye to move the mechanisms for driving the location of the OCT system on the sphere away from the face and eyes.
3) Displacing the center of sphere toward the eye to minimize the distance variation to the retina as one scans across the field of view.

In the case that the center of the sphere is displaced relative to the pupil location, it may become important to have an additional angular alignment capability between the surface that remains parallel to the sphere, and the axis of the OCT imaging system, which must point towards the pupil during the scanning. To maintain this alignment to the pupil, it may also be desirable to have a pupil tracking component mounted with the OCT imaging system that monitors the axis of alignment of the OCT system relative to the pupil and adjusts the angular alignment system to maintain the pointing of the OCT system to the pupil.

Figure 6:
FIG. 6 illustrates an exemplary guidance system for aiming an OCT imaging module (in accord with the present invention) at the pupil center.

FIG. 6 shows an example of such a system with a camera pointing along the axis, or a parallel axis, to the OCT system. That is, FIG. 6 provides an example of a guidance system for aiming an OCT imaging module at the pupil center of an eye 67. In the present illustration, a pupil camera and scan module (e.g., OCT system) are shown jointly embodied by element 61. Feedback from this camera would then be used to adjust the alignment system to align the camera to the pupil, and thus also align the OCT system to the pupil. That is, the pupil camera may track the center of the eye pupil, and drive (e.g., provide feedback signals to), for example, a 2-axis gimbal 63 that provides tilt functionality to maintain alignment of camera-and-OCT imaging module 61. In the present example, gimbal 63 is attached to a moveable scan module platform (or imaging module plate) 65 that preferably provides spherical motion (e.g., motion consistent with the surface of a sphere). In summary, the pupil camera tracks the pupil center, driving the 2-axis gimbal to maintain alignment of camera-and-OCT imaging module 61. Thus, pupil tracking may address both eye motion and misalignment due to the wide FOV pivot system. The present system can thereby maintain alignment over a predefined region (e.g., a 2×2×2 inch region), which is a much larger region within which a patient's eye needs to be placed to achieve effective imaging (e.g., the pupil box) than is traditionally required.

If the alignment system were sufficiently calibrated, one could also mount the camera directly to a parallel surface and then use the feedback to align the OCT system without also affecting the camera system. In case of cataracts, or other opacities in portions of the pupil, such a system could also maintain alignment to a specific location on the pupil to optimize image quality. In the absence of such opacities, the system would most likely maintain alignment of the OCT system to the center of the pupil.

Figure 7A:
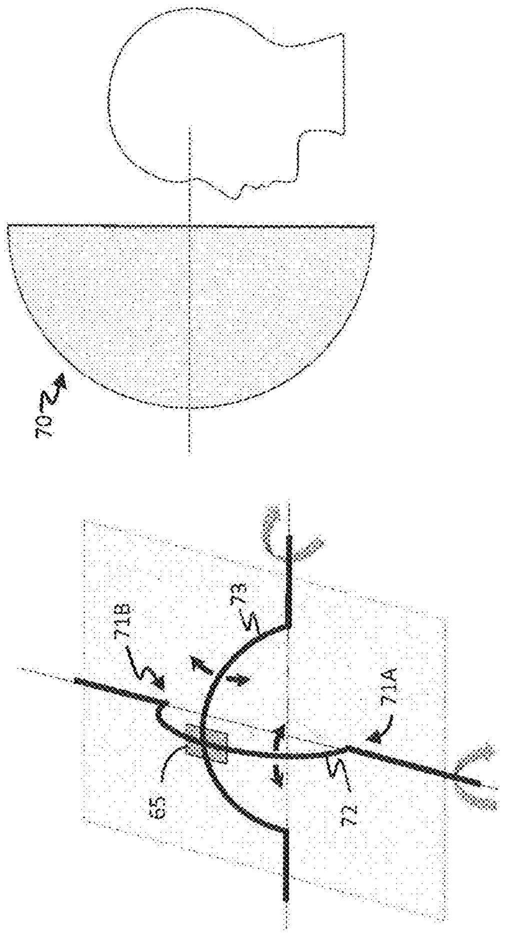
FIG. 7A is a pivot system for scanning an imaging module, and shows a structure for moving the imaging module along the surface of a sphere using one or more pivot points.

FIG. 7A shows a transport system that defines a spherical motion for an imaging module (e.g., pupil camera and/or scan module and or other medical imaging device). The transport system of the present embodiment includes a pivot system for scanning the imaging module in accord with the present invention where the acquisition angle is driven/defined by one more rotating struts (or rods) 72/73 whose rotation define a sphere (or spherical) plane/surface 70 (e.g., define spherical motion). FIG. 7A illustrates a particularly simple method of moving the imaging system (e.g., attached to imaging module plate 65) along the surface of the sphere (or partial sphere) by use of a pivot point 71A on the sphere, e.g., displaced 90 degrees relative to the axis of the eye, with a curved strut 72 extending from this pivot point 71A along the surface of the sphere to a second pivot point 71B on the opposite side of the sphere. Rotating the strut 72 relative to the two pivot points 71A/71B then causes the strut 72 to sweep across the surface of the sphere. If, as is shown, a second strut 73 is mounted at a 90 degree rotation on the sphere relative to the first strut 72, and also rotated in a similar fashion, the intersection of the two struts 72/73 can be placed at any point on the sphere. Thus, by mounting imaging module plate (or scan module platform) 65 to the intersection of (e.g., between) the two struts 72/73, one can create the desired behavior of a platform 65 that can be translated to all points on the section of sphere, with a surface on this platform 65 always parallel to the sphere surface, and thus having a perpendicular point to the center of the sphere where the pupil would reside. Note that although one would expect the best mechanical performance if the two struts 72/73 were rotated 90 degrees relative to one another on the sphere, the locations of the rotation points do not need to be 90 degrees apart. If the struts are not 90 degrees apart, all points on the sphere can still be reached, but the force generated by rotating one strut will not be directly along the axis of the other strut, creating some addition friction.

Figure 7B:
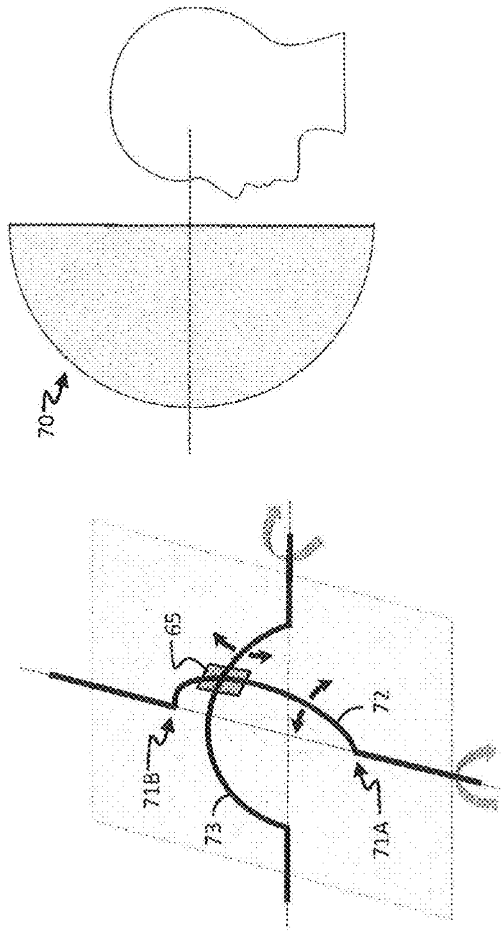
FIG. 7B illustrates the displacement of the imaging platform of FIG. 7A when the structure is rotated, or pivoted.

It may not be desirable for the pivot points to be at the same plane as the center of the sphere, where the pupil should reside. Since the face and body of the patient can also be in this plane, it can be difficult to put the pivot points at these locations without impinging on the human body. One solution, as mentioned earlier, is to move the sphere away from the body, moving both the pivot points and sphere center in front of the eye and body. If this is done, the OCT axis alignment system may need to correct for this offset, maintaining alignment to the pupil. This could be done either through a tracking system that causes the optical axis of the system to stay aligned to the pupil, or by putting an angle dependent offset on the alignment system that compensates for this displacement, or both. This capability to tilt and point the scan module is shown in FIG. 7B. That is, FIG. 7B shows the displacement of the platform when one of the struts is rotated.

Figure 7C:
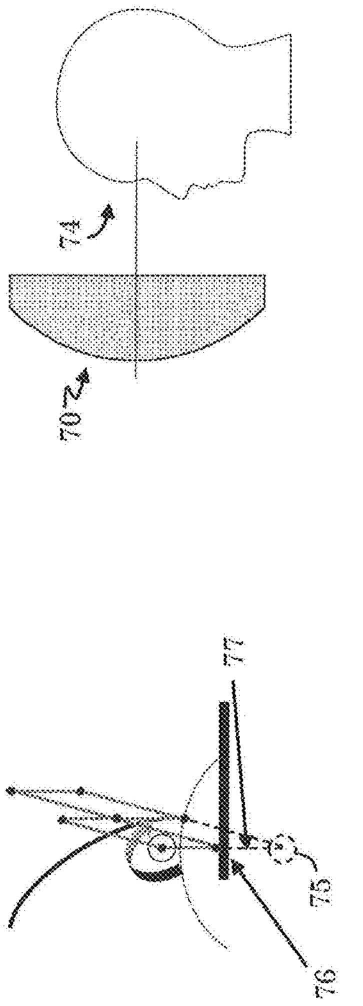
FIG. 7C is another pivot system for scanning an imaging module, and shows a mechanism for shifting the effective pivot point of FIG. 7A mechanically.
Figure 7D:
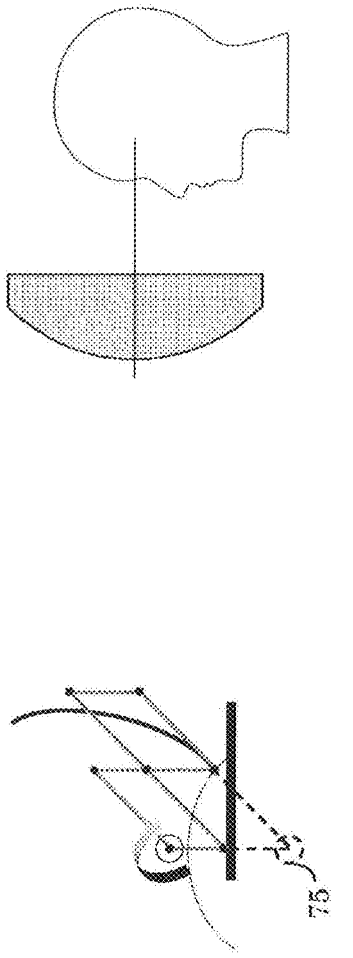
FIG. 7D illustrates the displacement of the imaging platform of FIG. 7C when the structure is rotated, or pivoted.

Alternatively, one can shift the effective pivot point mechanically. One such example of a mechanical shift to the pivot point is shown in FIG. 7C. In this way, the clearance from face 74 can be improved by shifting pivot point. In this diagram, the effective pivot point (e.g., pivot point 75) is shifted relative to location 76 by a given distance 77. Shifting the pivot point in this, or a similar, manner enables one to use a smaller portion of the sphere, while also moving the rotation mechanism away from the face 74. FIG. 7D shows the displacement of the platform when one of the struts is rotated.

Figure 8:
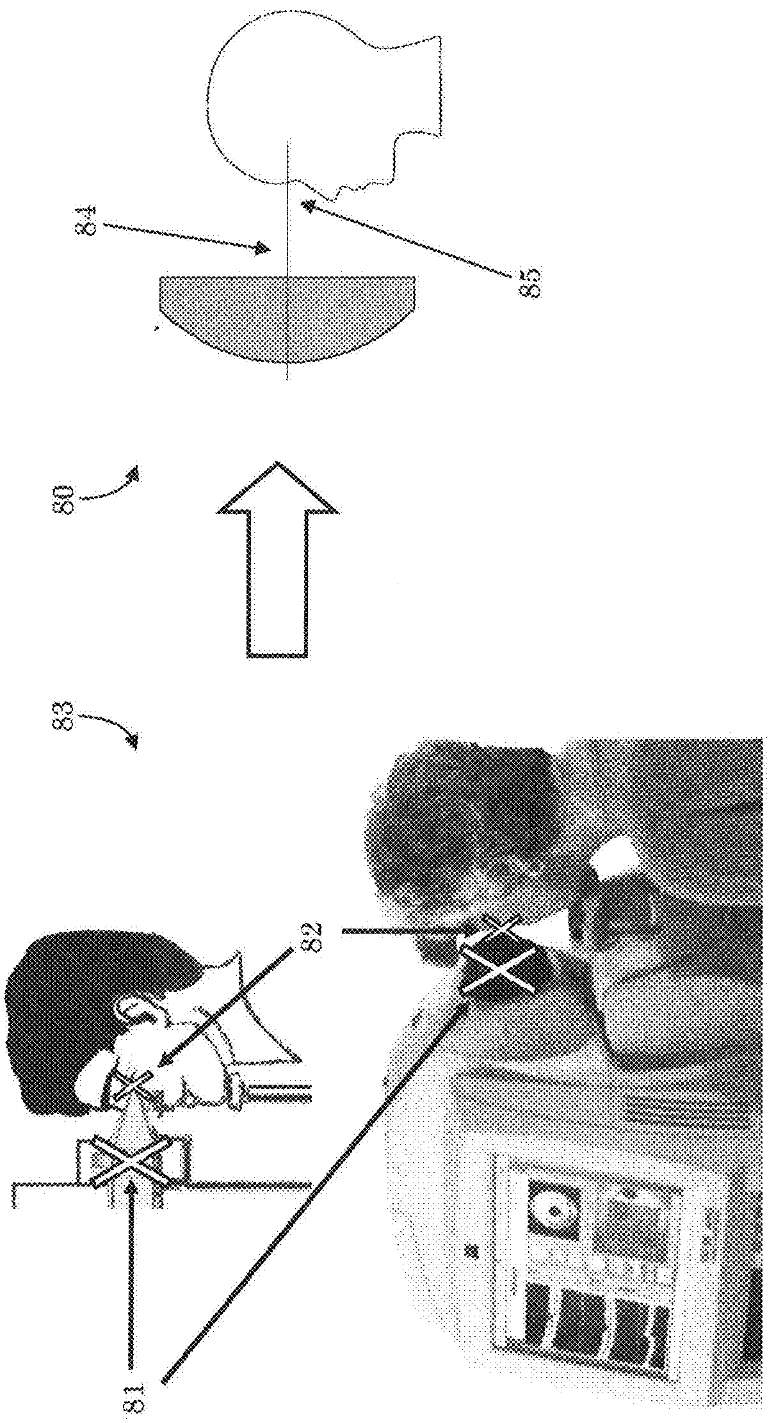
FIG. 8 illustrates that the present invention may eliminate, or reduce, the need for the highly limited area known as the "pupil box" and optionally also the ophthalmic lens.

This approach, wherein a small FOV system is moved in an arc around the pupil while maintaining alignment to the pupil has an additional advantage in that it greatly reduces the need for placement of the pupil in a highly limited area, known as the "pupil box", defined by the optics of the system. FIG. 8 shows that the present system 80 eliminates the wide field ophthalmic lens 81 and corresponding pupil box 82 requirements of a traditional optics system 83. The pupil box 81 may traditionally define a three-dimensional region of space (relative to the ophthalmic device) within which a patient's pupil should reside to achieve effective imaging. While one could theoretically add pupil tracking that moves the optics in a traditional wide field system 83, the size and weight of the optics needed to support the wide FOV imaging makes this impractical. By contrast, the present system provides no optics near the eye (indicted by arrow 84) and flexible pointing of the optics eliminate the pupil box (as indicated by arrow 85). The approach described above, with its much lighter weight limited FOV optics, enables tracking of the pupil by moving the optical system. It is particularly applicable in wide field (>50 degree) imaging systems, where moving of the heavy optics head for pupil tracking becomes impractical.

Figure 9A:
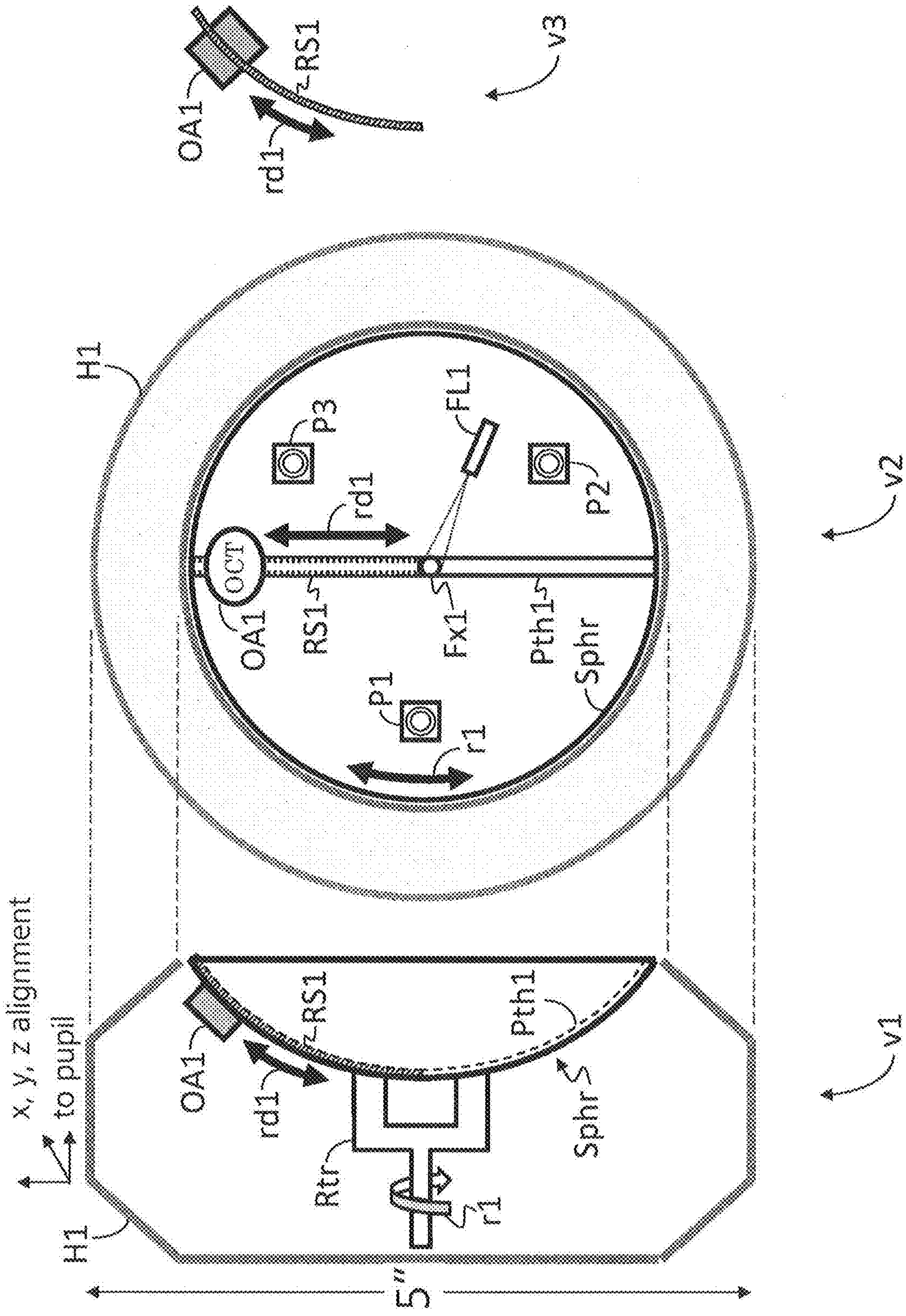
FIG. 9A illustrates another approach to physically moving the scanning system (or "OCT assembly" OA1) to scan across the eye through the use of a polar coordinate-based system.

FIG. 9A illustrates another transport system in accord with the present invention for defining a spherical motion for an imaging module. Like described above, the present transport system physically moves the scanning system/imaging module (or "OCT assembly" OA1) about a spherical plane/motion to scan across the eye, but the present embodiment includes a polar coordinate-based system. In the present example, the above-described spherical motion of the OCT assembly OA1 is provided by a spherical (or partial dome-shaped) surface or frame (Sphr) within a housing H1. Optionally, surface Sphr may minimally be of sufficient size for receiving a patient's eye, and may therefore be relatively small as compared to a typical macroscopic OCT system. In the present example, housing H1 is illustratively shown to be five inches (12.7 cm) tall. FIG. 9A provides an internal side-view (or cutout view) v1 of housing H1, a frontal view v2 of housing H1, and an exploded-view v3 showing a portion OCT assembly OA1 extending from the exterior of surface Sphr to its interior along a curved radial slide (or guide) (RS1), which may be disposed along the interior, curved plane of surface Sphr. A rotor Rtr, or other rotating armature/mechanism, may rotate surface Sphr (e.g., about the axial center of a patient's pupil), as indicated by arrow r1. In this manner, OCT assembly OA1 may be made to rotate unidirectionally or bidirectionally along a circular path (e.g., azimuthal direction) at a given radial distance from the center of surface Sphr. Additionally, OCT assembly OA1 may be made to move radially (outward or inward) from the center of surface Sphr along radial slide RS1 (or other radially movable carriage/holding-assembly or rail system), as indicated by arrow rd1. By a combination of rotor Rtr (rotating surface Sphr) and radial slide RS1, OCT assembly OA1 may be positioned at any location along the spherical plane defined by the interior of surface Sphr.

Figure 9C:
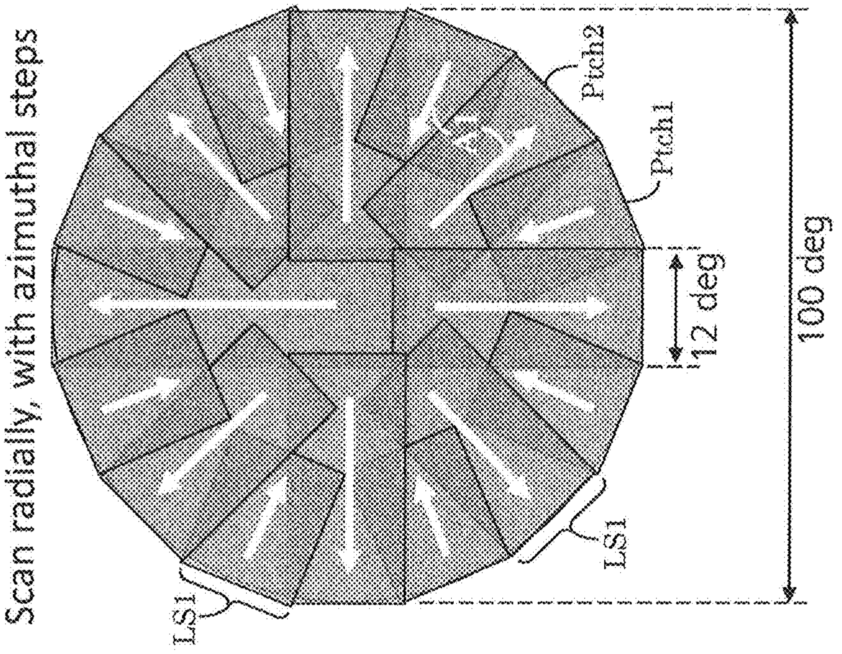
FIG. 9C illustrates an exemplary scan pattern suitable for a spherical scanning assemblies, particularly for OCTA scanning.
Figure 9B:
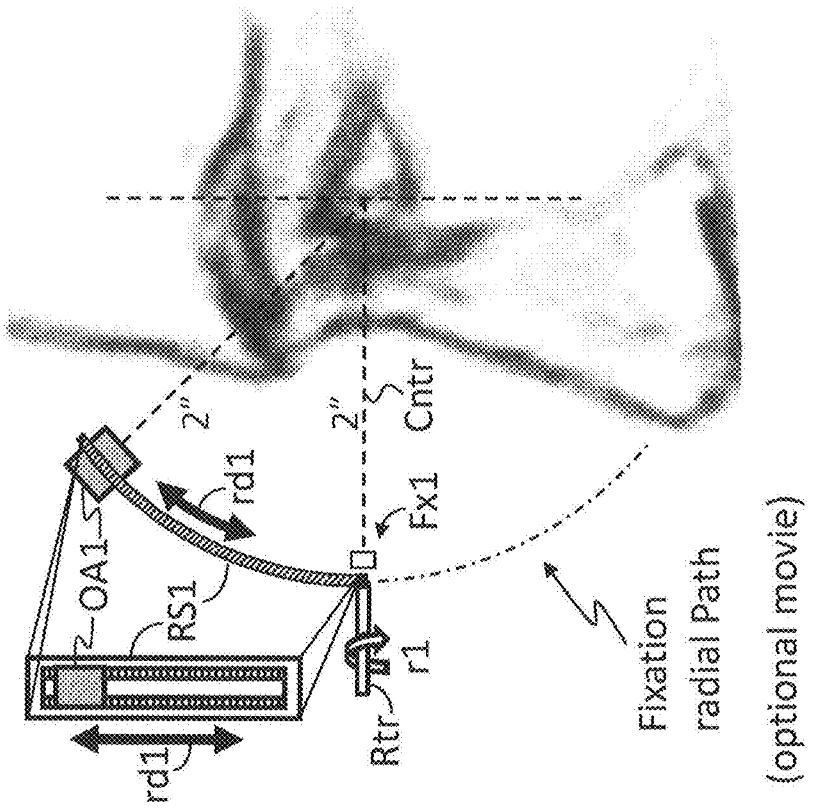
FIG. 9B provides a close-up, frontal view of radial slide RS1 relative to a patient's eye.

FIG. 9B provides a close-up, frontal and profile view of radial slide RS1 relative to a patient's eye. In the present example, OCT assembly OA1 is shown to have a rectangular frontal profile, while in the example of FIG. 9A, OCT assembly OA1 is shown to have a circular frontal profile. It is to be understood that OCT assembly OA1 is not limited to any one configuration. As shown, radial slide RS1 may rotate azimuthally (e.g., by means of rotor Rtr, or other rotating shaft, as indicated by arrow r1) about the center of a patient's pupil (as indicated by dotted line Cntr) such that OCT assembly OA1 may be moved to any position within the spherical surface defined by surface Sphr. In this manner, OCT assembly OA1 may be maintained a fix distance (e.g., two inches or 5.08 cm) from the patient's pupil. In the present example, a fixation target Fx1 (e.g., a mirror, light emitting diode, miniature electronic display, etc.) is fixed to the center of spherical surface, which is aligned with the patient's pupil. Optionally, the fixation target Fx1 may be made to move to (or be fixed at) any other desired position along surface Sphr.

Returning to FIG. 9A, fixation target Fx1, which may be a mirror, is shown at the center of surface Sphr, and may be provided by means of a fixation laser FL1, which eliminates the need for focus adjustment of the fixation target Fx1. Fixation laser FL1 my project a still or moving image (e.g., movie) on the fixation target Fx1. Optionally, fixation target Fx1 may be attached to surface Sphr and rotate with it, or be maintained at a fixed rotation relative to the eye. Furthermore, fixation laser FL1 may be independent of surface Sphr and project the fixation target Fx1 at any interior location on surface Sphr, such as if the interior of surface Sphr is reflective, e.g., has a mirror surface. In this manner, fixation laser FL1 may project fixation target Fx1 at multiple fixed locations relative to the patient's pupil while surface Sphr rotates. or may define a fixation path Pth1, such as a radial path opposite the radial path rd1 of the OCT assembly OA1. Other elements, such as pupil alignment cameras P1, P2, and P3 may be attached to the spherical surface Sphr and rotate with it.

FIG. 9C illustrates an exemplary scan pattern suitable for a spherical scanning assemblies, particularly for, but not limited to, OCTA scanning applications. Multiple scanning regions, or patches, (Ptch1/Ptch2) may be created in radial and azimuthal steps to define a composite, circular scanning region. For example, if the OCT assembly has a limited scanning field of view of, for example, ±6 degrees, then each scanning patch may have a limited scanning width (LS1) of 12 degrees. As shown, the scanning patches may consist of shorter scanning patches Ptch1 and longer scanning blocks Ptch2, directed radially and overlapping each other to define an effective (e.g., composite, such as by montaging) larger field of view of, for example, 100 degrees. As indicated by inward-pointing and outward-pointing arrows A1, some scanning patches (e.g., shorter scanning patches Ptch1) may be scanned as the OCT assembly is moved radially inward toward the center of the spherical surface, while other scanning patches (e.g., longer scanning patches Ptch2) may be scanned as the OCT assembly is moved radially outward from the center of the spherical surface. In this manner, continuous azimuthal and radial scanning by one or more scanning beams may be achieved. Optionally, if the entire scanning area/region defined by a patch Ptch1/Ptch2 is defined by the scanning field of view of the (e.g., stationary) OCT assembly, then a scanning patch Ptch1/Ptch2 may be scanned while the OCT assembly is at a corresponding stationary location, before the OCT assembly is moved to the next scanning position to capture the next scanning patch. As mentioned above, the OCT assembly may be comprised of one or more single point scanners, line scanners, or full-field scanners. If the OCT assembly includes multiple scanning beams operating in parallel, such as discussed above, the effective scanning speed of the system may be increased.

Although one could do any combination of radial and azimuthal motion to scan the eye, if the OCT system is parallelized such that there are multiple OCT scan beams entering the eye, and one is interested in OCT angiography, it may be desirable to take a series of radial scans with azimuthal rotation between them, as shown in FIG. 9C, so as to keep the rotation of the array fixed during each radial scan. In particular, this would ensure that there is no rotation between repeat angio scans, as such rotation would change the horizontal and vertical spacing between parallelized beams, and thereby make it difficult to repeat the A-scan pattern (at the same location) for angiography.

In some ways the approach described above is similar to montaging, where one manually takes a set of images with a limited field of view instrument, and then combines them to generate a wide field of view image. In such a manual approach, one typically asks the patient to look at a fixation target, and then takes the series of images with the fixation target at different locations. The eye is then looking in a different direction for each image, and thus the photos show different parts of the eye that can then be montaged. The approach described herein is different both in that the fixation target is not moved between collections of the subfields, and in that all of the subfields are acquired sequentially with no need for alignment steps between the acquisitions of the subfields.

Figure 10:
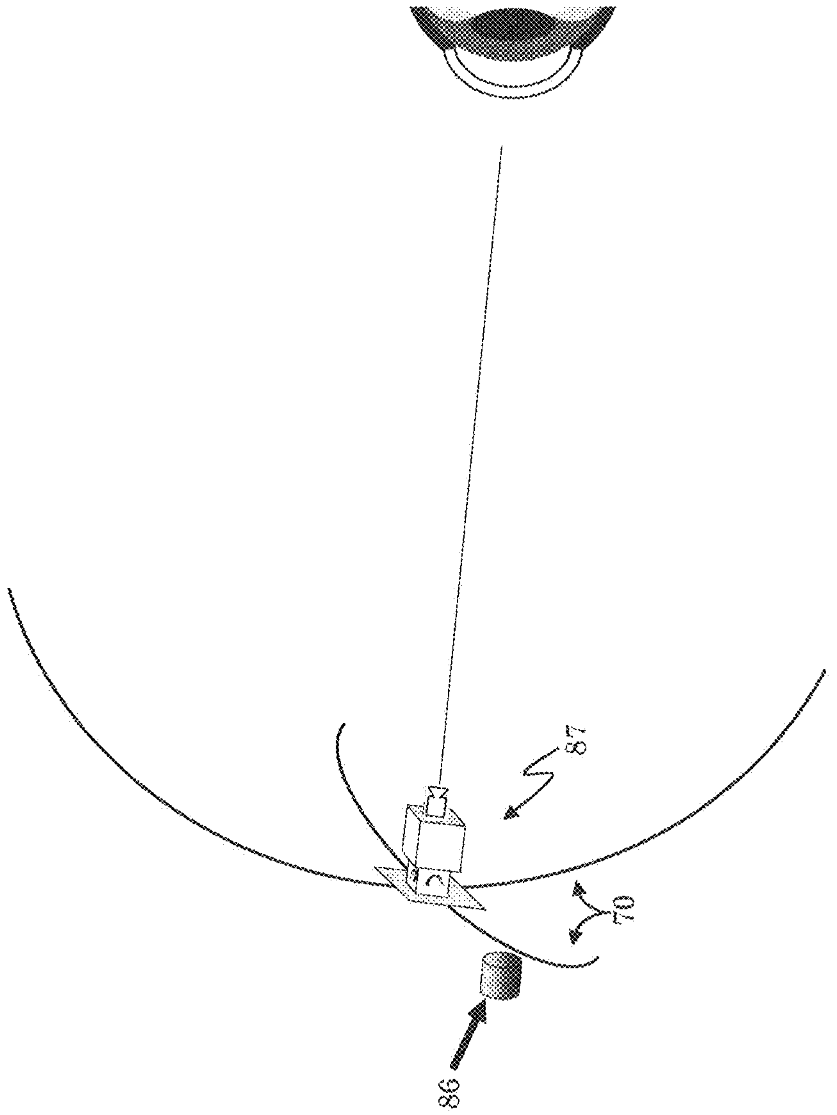
FIG. 10 illustrates the placement of a fixation target behind the spherical plane that the present imaging system transverses.

One challenge for montaged images is that the fixation target is within the imaged field of view for the central image, but not for the peripheral images. This may lead to a need for two fixation target systems, one within the field of view of the optics, and one external to the optics. In the present system, this issue can be avoided, only requiring one fixation target system to cover both central and peripheral subfields. This can be accomplished by placing the fixation target 86 behind the spherical plane 70 that the imaging system (e.g., scan module or scan head) 87 transverses, as shown in FIG. 10. The small scan module 87 may briefly block fixation target 86 as the scan module 87 passes in front of fixation target 86. That is, the fixation target 86 is occasionally blocked when the imaging system 87 passes in front of it, but as fixation targets are often designed to blink, one can set the blinking pattern such that the fixation is off when the imaging system 87 briefly blocks it. This approach also simplifies the system by eliminating the need for optics to combine the fixation target and imaging systems. One could also have multiple fixation targets (not shown) at different locations behind the scanning optics to generate more classic montage images, where multiple images are acquired with different fixations, and then combined. This could be done either with separate complete acquisitions for each image, or where one target is illuminated followed by the next during the acquisition. If one is going to have different fixation locations during a single image acquisition, a preferable approach may be to have a single fixation target that moves during the acquisition to expand the field of view obtained by the system. The single fixation target for both within the field of view of the image optics and external to this field of view makes this possible.

Figure 11:
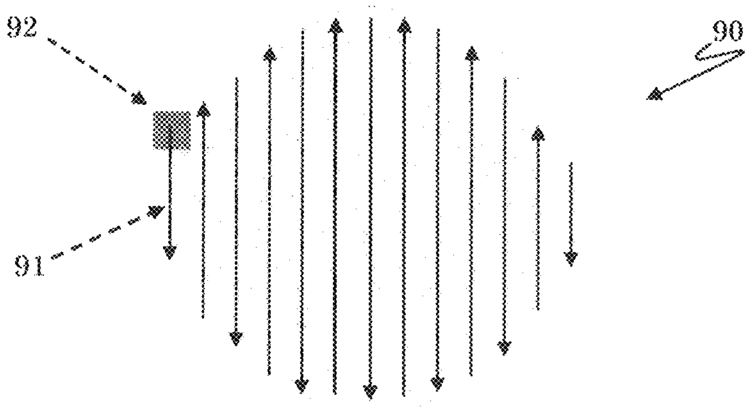
FIG. 11 illustrates the acquisition of limited fields of view sequentially by translating the present scan module.

FIG. 11 shows a scanning pattern 90 where the scan module's scanning (or acquisition) field of view defines a region of interest 92, and arrows 91 illustrates the translation of the scan module to define region of interest scanning, which enables optimized OCT imaging. This illustrates another advantage of the present system relative to classic scanning systems, which is that by acquiring (scanning) limited fields of view sequentially by translating the scan module, the system moves relatively slowly across the retina, making it possible to adjust the imaging parameters of the system during the acquisition to account for the variation in the optical characteristics of the retina across the field of view. The parameters that could be adjusted during the acquisition include, but are not limited to, the scan depth, focus, astigmatism, polarization, aberrations, and scan range.

As the OCT typically uses near infrared light for the imaging, which does not significantly bother the patient, it is possible to acquire data over a significant period of time, up to 30 seconds or more. However, motion of the retina during the acquisition can become a challenge, creating distortions in the image and/or regions of the eye with missing OCT data. To address this, one often uses a second imaging system to track the retina, as is done in the Heidelberg Spectralis' and Zeiss Cirrus' OCT instruments. There has also been a relatively recent development in OCT known as OCT angiography, whereby the microvasculature in the eye is imaged by detecting the motion of the blood through repeat scans. It is herein proposed that these two capabilities can be combined with the present new scan approach by using the repeat scans to both detect the flow of blood in the eye, and to measure the overall motion of the retina. Historically, OCT angiography has been done by repeating single B-scans, each consisting of a long (10-60 degree) line scan across the retina, where each B-scan takes roughly 5 msec to acquire. When the retina moves, these acquisitions do not overlap, and information from the secondary tracking system is then used to correct the position of the OCT scan and retake the data. In the present case, by acquiring limited 2D (two dimensional) regions of the eye over these 5 msec periods rather than a 1D (one dimensional) line, the present system can detect the motion in 2D by identifying the A-scan in the 2D region that matches the repeat scan. As a simple example, if one has a 500 k A-scan/sec system, with a 5 msec delay between repeat scans, one can scan a 50×50 A-scan region, corresponding to roughly 50*20 um=1 mm×1 mm region, and thus be able to track motion up to 1 mm per 5 msec. Thus, the present scanning approach enables one to use the same repeat scans both for OCT angiography and retinal tracking, making retinal tracking without a secondary tracking system possible.

In certain cases, it may also be desirable to have a micro-optics-based OCT system without a transverse scan capability, where the transverse scanning would be provided by moving or rotating the micro-optics OCT. For example, one could configure a micro-optics OCT module without an onboard beam scanner, and instead one drags/moves the micro-optics OCT module (and its non-scanned OCT light beam(s)) across the surface of the skin in order to generate a B-scan of the skin tissue. Such a system could either include optics external to the micro or semiconductor optical bench for coupling the light to the sample, or could directly illuminate the sample, without any additional optics. Similarly, there are applications where the micro-optics system could be used without scanning in an optical coherence domain reflectometry mode. One example of such an application could be measurement of distance to a sample in a microscope so as to optimize the focus of the microscope.

A further aspect of an OCT system that can be integrated as part of the micro package is the focus adjustment. Tunable lenses, sometimes also called liquid lenses, have been demonstrated to provide very quick focus adjustment, but are typically limited in their clear aperture. The small beam diameters inside the micro package or in close proximity to the micro package are therefore a great match to such tunable lenses. In a preferred embodiment the focus tunable lens would be placed in a pupil conjugate plane.

Broader spectral tuning bandwidths can be achieved using MEMS tunable VCSELs. These devices are tuned by adjusting their cavity length with the help of a MEMS element. They exist in optically pumped and electrically pumped varieties. Optically pumped tunable MEMS VCSEL usually include at least a laser diode for optical pumping and the MEMS VCSEL. An electrically pumped tunable MEMS VCSEL usually include at least a MEMS VCSEL with an active gain section that is driven electrically. Both electrically and optically pumped VCSELs are often combined with an optical amplifier to increase the optical power. Optionally, MEMS tunable VCSEL may be co-packaged with the aligned optical amplifier. Silicon (e.g., semiconductor) optical benches may use different approaches for alignment. For example, a microscope and image recognition may be used, and/or a laser beam may be sent through the system and its position or intensity optimized. These components are typically either packaged separately and fiber coupled to each other or co-packaged on a micro bench inside a butterfly package. Their manufacturing process involves several active alignment steps and per device fiber coupling and packaging steps. To further lower the size and cost of these devices as well as to enable the manufacturing of larger volumes of these devices, it would be beneficial to build such devices on a silicon (semiconductor) optical bench relying on passive placement and alignment steps in order to profit from the scalability of wafer level manufacturing and packaging processes.

VCSELs, detectors, and pinholes can all be manufactured at the wafer level as arrays with sub-millimeter/micron spacing between the elements of the arrays. Therefore, a parallel micro or semiconductor optical bench OCT system may be configured where the VCSELs, detectors, and/or pinholes are arrays, and the array of light beams from the VCSELs propagate through the individual optics of the micro/silicon bench in parallel (multiple OCT optical beams passing through the same optical components, where each beam has at least one corresponding detector for generating OCT signal.) As an example, assuming a 3×3 array of VCSELs, with corresponding arrays of detectors and pinholes, one could go from one acquisition channel to 9, with all 9 channels sharing the same lenses and mirrors, and therefore no need for additional optics in the OCT interferometer. One could also do this with a 1D array of VCSELs, which might be a more natural pattern for scanning, but would be less efficient in terms of filling the lenses, which typically have a circular aperture for the optical beam(s) to pass through. It is desirable to pack as many beams as possible into a given size set of optics, with whatever pattern gives you the maximum packing. For instance, one might want a hexagonal packing with rows of 2, 3, 2=7 beams, or 3, 4, 5, 4, 3=19 beams. As mentioned above, the optimum arrangement of beams to pass through the optics might be different than the arrangement of beams desired for scanning. In such a case, one could change the arrangement of the beams between the OCT interferometer and the scanning mirror with one or more optics that deflect each beam appropriately.

Figure 12:
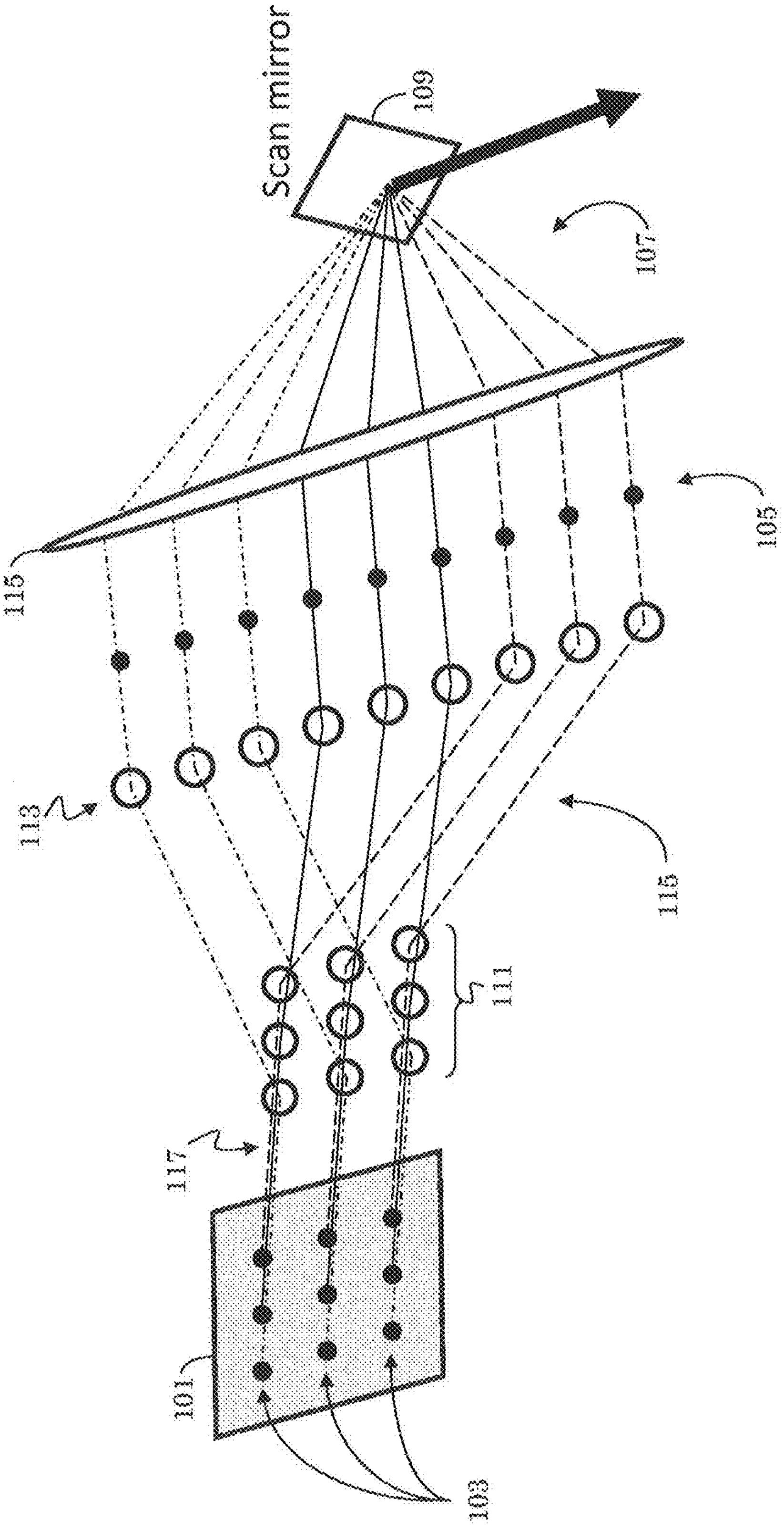
FIG. 12 illustrates a configuration where the beams incident on the scanning mirror are a line of beams all hitting the scanning mirror at the same location, but coming in from different angles along a line.

FIG. 12 illustrates a configuration for converting a 2D array (e.g., a 3×3 array) of light beams 101 (black dots 103 represent focused beams) to a 1D array of light beams (e.g., represented by black dots 105). The (collimated) beams 107 incident on the scanning mirror 109 are a line of beams all hitting the scanning mirror 109 at the same location, but coming in from different angles along a line. Given the 2D array of beams 101 in the OCT interferometer, one would want optics between the OCT interferometer and scanning mirror 107 that convert the 2D array of beams 101 to the 1D array as shown in FIG. 12. In the present example, a 2D array of lenses (with beam deflection) 111, 1D array of lenses (with beam deflection) 113, and lens 115 provide this conversion. Converging/diverging beams 117 are transferred between 2D array of beams 101 and 2D array of lenses 111. Collimated beams 115 are transferred between 2D array of lenses 111 and 1D array of lenses 113, and converging/diverging beams 105 are transferred between 1D array of lenses 113 and lens 115.

Figure 13A:
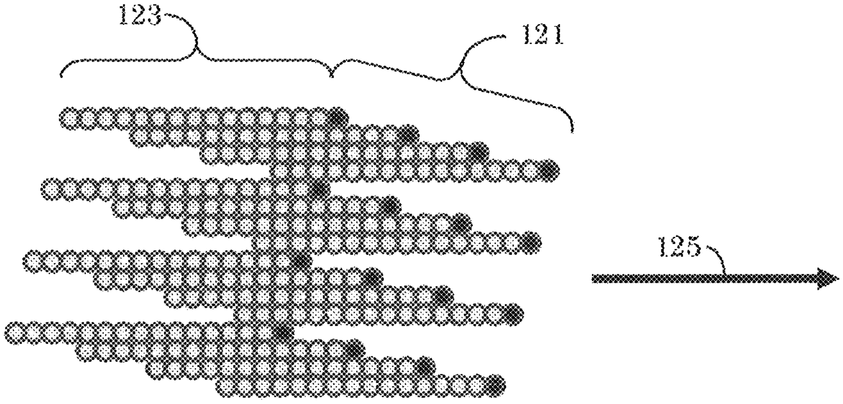
FIG. 13A illustrates another way to convert a 2D array to a set of points with equal spacing along the vertical direction by slightly rotating the array.
Figure 13B:
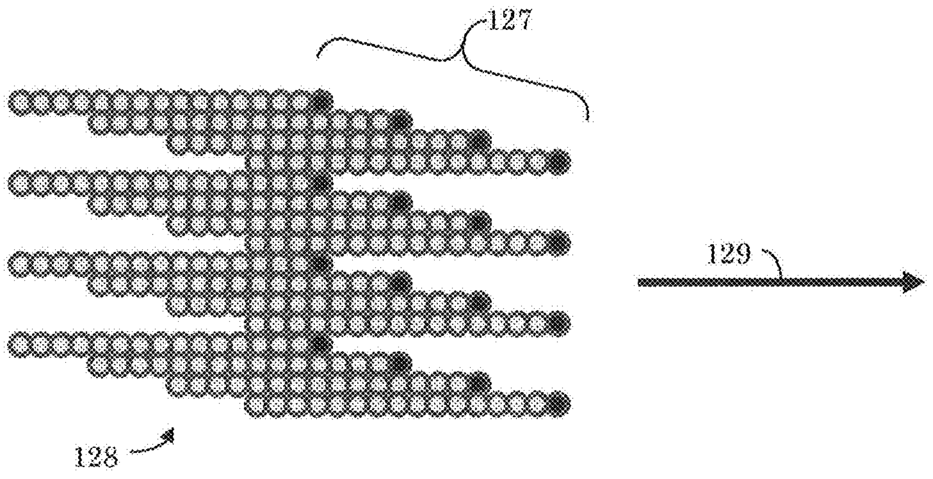
FIG. 13B shows another way to achieve an effect similar to that of FIG. 13A with an array of VCSELs in the form of a parallelogram, with each row or column shifted slightly perpendicular to the scan direction.
Figure 13C:
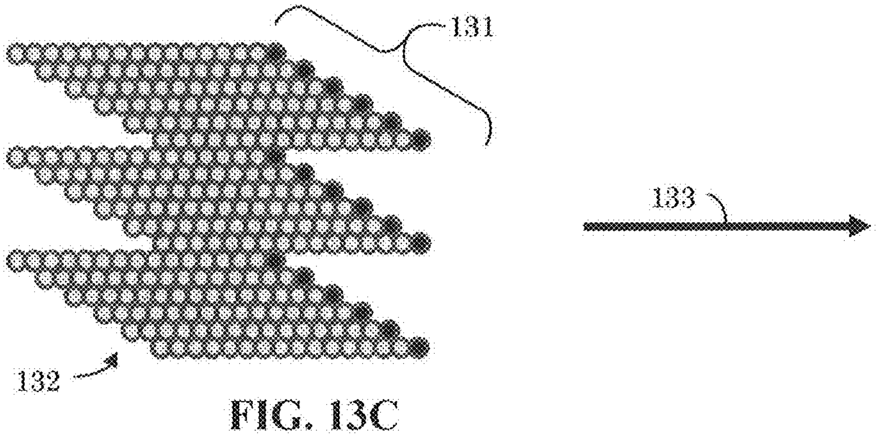
FIG. 13C illustrates that the number of VCSELs in the vertical and horizontal directions may differ significantly.

With reference to FIG. 13A, another way to convert a 2D rectangular array of points 121 to a set of points with equal spacing along the vertical (transverse to scanning) direction is to simply rotate the array slightly relative to the scanning direction, as shown. The black dots represent the rotated 4×4 array of points 121, the gray dots 123 represent scanned points (e.g., the resulting scan pattern), and arrow 125 indicates the scan direction. With reference to FIG. 13B, another way to achieve a similar effect is with an array of VCSELs 127 arranged in the form of a parallelogram, with each row or column shifted slightly perpendicular to the scan direction 129. Again, the grey dots 128 indicate scanned points. With reference to FIG. 13C, a parallelogram array 131 with different horizontal and vertical VCSEL spacing is shown. As before, the grays dots 132 indicate scanned points. Arrow 133 indicates the scan direction. To maximize the use of the clear circular aperture of the lenses, it is desirable to have the 2D array be roughly square (nearly equal height and width of the array). As the spacing between the VCSELs 131 may differ significantly in the horizontal and vertical directions, the number of VCSELs in the vertical and horizontal directions may differ significantly to achieve this.

Figure 14A:
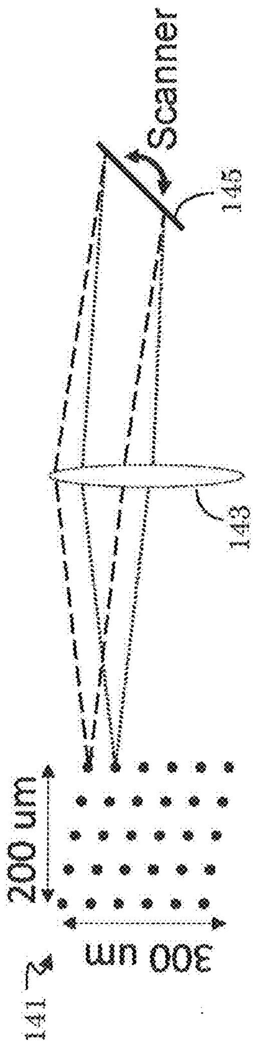
FIGS. 14A and 14B show passing a beam array through a lenslet array (or lens array) to adjust the quantity of the numerical aperture times the pitch to optimize the imaging on the retina.
Figure 14B:
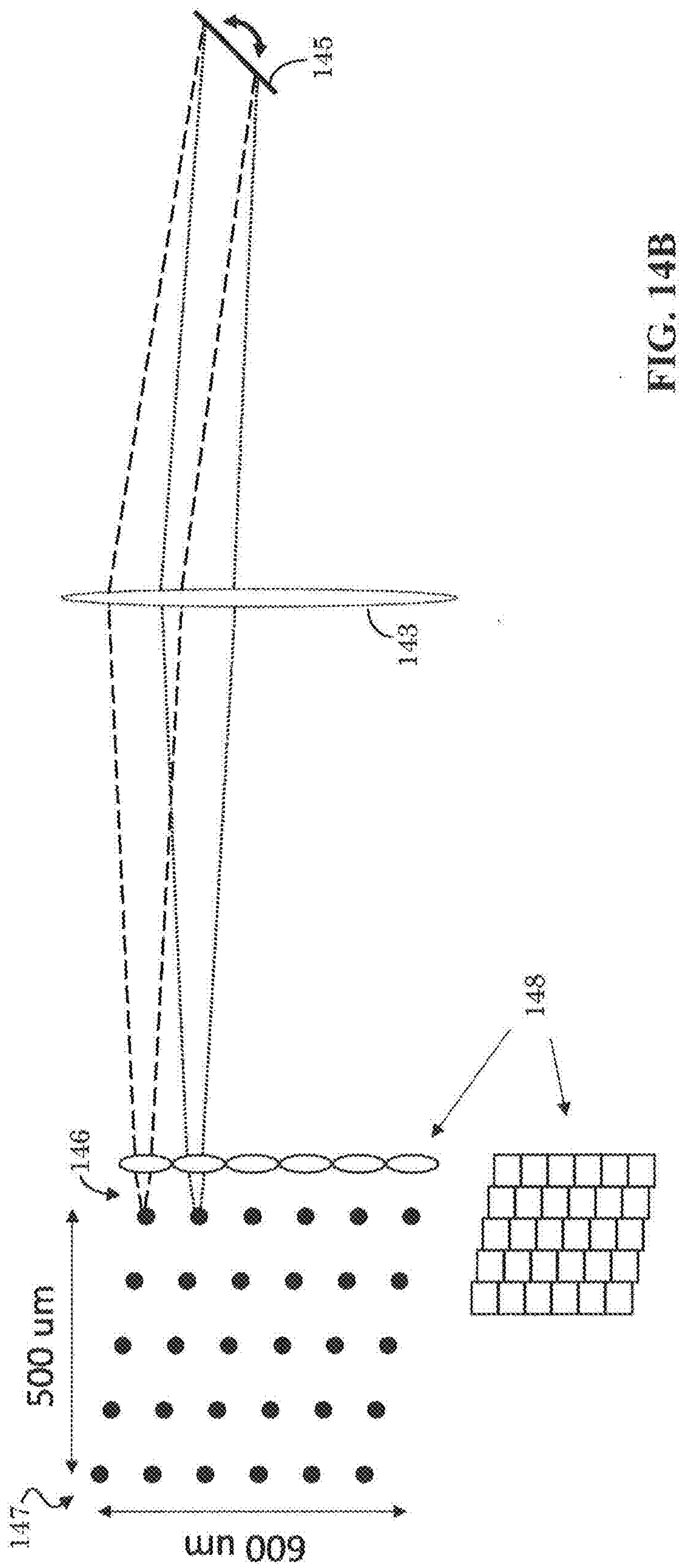

The VCSEL arrays will have a given pitch (spacing between VCSELs) and beam numerical aperture (e.g., a dimensionless number that characterizes the range of angles over which the system can accept or emit light). The numerical aperture times the pitch remains a conserved quantity when one images the VCSEL with single element optics. FIG. 14A provides an example of a VCSEL array 141 (e.g., of size 200 μm×300 μm) with a single lens 143 between it and a scanner 145. However, the desired “pitch” or “sampling spacing” times “beam numerical aperture” on the retina may not match this conserved quantity from the VCSEL array. To address this, it may be necessary to pass the beam array 146 (e.g., from a 500 μm×600 μm VCSEL array 147) through a lenslet array (or lens array) 148, as shown in FIG. 14B, thus adjusting this conserved quantity to optimize the imaging on the retina. In the example of FIG. 14B, lens array 148 reduces the divergence of beams, increasing the distance to the lens. The transverse spacing between beams at lens array is unchanged, but lens focal length and distance from lens to scanner (mirror) 145 is increased.

The use of VCSEL arrays increases the total optical sample power of the device according to the number of VCSELs in the array. This allows each individual channel to use lower sample power than typical single beam OCT systems and still achieve equal or better image quality and/or imaging speed. In particular, it enables the use of VCSELs for high quality OCT imaging of biological samples without optical amplifiers, which has otherwise not been demonstrated.

Although omitting all fiber optics or other waveguiding optics was described as advantageous in several of the above embodiments, some micro-optic OCT systems may include waveguides, for example as part of edge emitting lasers, semiconductor optical amplifiers or optical modulators. Micro-optic OCT systems may further be an assembly of multiple planar waveguides and/or photonic integrated circuits (PIC) coupled together using micro-optics. For example, a semiconductor optical bench assembled using wafer level assembly and packaging steps, may represent a cost-effective way to combine and package multiple optical components made from different materials, in a miniature hermetically sealed package. This is especially desirable in cases, where different components cannot be integrated on a single PIC, due to incompatible materials, e.g. when combining lasers or amplifiers made of GaAs with passive silicon nitride PICs. A micro-optic OCT system may further lend itself to include electronics in the same package, discrete analog electronic components, but also electronic integrated circuits. Especially systems built on a silicon optical bench, i.e. a silicon wafer, can enable a particular deep electronic and optical integration, as the same silicon wafer may be processed to include electronic integrated circuits. Such a system can then include not only passive and active optical components, but also electronic integrated circuits for driving light sources, signal conditioning, analog to digital conversion, signal processing (e.g. image reconstruction), data transfer and data storage.

In hybrid PIC/micro optic devices the micro optics may not only take the role of coupling between waveguides and/or photonic integrated circuits as described above. In some systems it may be desirable to implement some functionality of the system using micro optics and others using photonic integrated circuits, which would then reside on a common substrate and be co-packaged.

Further cases where fiber optics may be desirable, include an external light source fiber-coupled to the micro-optics assembly or fibers collecting the light in the detection arm and directing it to external photodetectors. The fiber in these cases may for example be single mode fiber, polarization maintaining fiber, polarizing fiber, or dual cladded fiber.

Although the micro-optics described herein are illustrated as having light propagating only in a single plane, it may be desirable to direct at least one of the optical beams for example in a direction perpendicular to this plane. It may for example be desirable to have the sample arm or sample and reference arm exit through the lid of the package instead of its sidewalls. The lid would in such an instance be transparent at the operating wavelength or include a window or lens integrated in the lid.

In summary, some of the innovations/features provided in the present application include:

1) Implementation of various aspects of the OCT/OCDR system on a micro optical bench or semiconductor optical bench
2) Implementation of hybrid systems, where some macroscopic aspects of the OCT/OCDR (e.g., sample arm and reference arm) are external to the micro or semiconductor optical bench, and the rest of the OCT/OCDR system is incorporated onto the micro-bench
3) Inclusion of components on the micro or semiconductor optical bench beyond just the OCT/OCDR interferometer, for instance including the scanning capability, potentially through the use of a micro-electro-mechanical systems (MEMS) mirror either installed on the bench, or integrated into the semiconductor bench through semiconductor manufacturing processes.
4) Use of the optical components of the OCT/OCDR system as part of a hermetic sealing of the micro or semiconductor optical bench to minimize optical surfaces. For example, if the transmission of the light from the micro or semiconductor optical bench to the outside world is not done through fiber optics, then the light must pass through a transmissive element in transitioning from the hermetically sealed OCT/OCDR engine to the external world. Instead of using a window for this transmissive element, as shown as W in FIG. 2B, one could place the quarter-waveplates at this transition between the hermetically sealed OCT/OCDR engine and the external sample and reference arms, as shown in FIG. 2A. The quarter-waveplates then can become part of the hermetic sealing, eliminating the need for the windows, W, shown in FIG. 2B. For different configurations of the OCT/OCDR, other optical components needed for the operation of the OCT/OCDR may also be used at this transition point for the hermetic sealing.
5) Creation of a free space optics OCT/OCDR system without the need for active alignment (other than any parts residing off the bench such as possibly the reference and sample arms) is also shown. This is particular achievable with a semiconductor optical bench given the extremely high accuracy of the placement of the components. The semiconductor optical bench's receptacle openings can be designed to hold components in predefined alignment orientations with high precision.
6) The assembly of a multitude of semiconductor optical bench OCT/OCDR systems may be packaged, and/or tested at the wafer level.
7) Integration of additional IC electronics (for instance, detector electronics and analog-to-digital converters) into the (e.g., silicon substrate) semiconductor optical bench package may further reduce cost and enable ultrashort electrical pathways to enable high speed electronics needed for ultrafast OCT/OCDR systems. For example, integrating circuits constructed onto the substrate of the semiconductor optical bench itself may avoid signal propagation delays and timing issues associated with routing traces/wires for interconnecting external, discrete components, and thereby achieve higher clock speeds.
8) If one were to integrate the detectors into the wafer, one could configure the polarizing beam-splitters to deflect the detection path beam from the horizontal down into the integrated detectors as shown in FIG. 3. Likewise, a VCSEL integrated into the semiconductor bench could emit light vertically directly out of the bench and be coupled back to the OCT/OCDR system on the bench through a turning prism.
9) Mixing of the analog OCT/OCDR signal with an adjustable frequency (e.g., a modulating reference frequency) oscillator would enable a rapid, all electronic path length adjustment. For example, the analog output from a detector may be mixed with a self-adjusting oscillator to demodulate the analog output to a target frequency range, and thus establish a desired image detection range. The self-adjusting oscillator may be digitally set (and/or controlled by a feedback mechanism) to achieve a target mixing frequency and thereby achieve rapid Z-tracking. This approach would also avoid the creation of Doppler shifts when changing the sampling depth.
10) Transmission of the returning light from the reference arm and/or sample arm may be passed through one or more pinholes to eliminate unwanted light that will not interfere appropriately (particularly multiply scattered light from the sample.)
11) Transmission of the light returning from the reference and sample arm may be passed through a shared pinhole. This causes mode matching between the reference and sample arm light to maximize the interference between the arms. This could be done either before or after the interference occurs (for example before or after PBS1 in FIG. 2A.) Doing it before the interference, as shown in FIG. 2A, has the benefit for balanced detection systems that only one pinhole is required, rather than one in front of each of the two detectors. In addition to reducing the number of required pinholes, this can also improve balanced detection as using the same pinhole for light reaching both detectors creates consistency in the spatial filtering of the light reaching the two detectors. Alternatively, the photodiode(s) itself could act as pinhole(s). To achieve this, for example, the diameter of the photodiode(s)'s active area may be made close to the diameter of the focused spot.
12) A quadrature detector may be implemented on the present micro or semiconductor optical bench without the need of active alignment.
13) The micro or semiconductor optical bench OCT/OCDR system may form a handheld OCT/OCDR system without fiber optics or semiconductor waveguides.
14) The micro or semiconductor optical bench may contain all optical components of the OCT system other than aspects of the sample arm, thus eliminating the need to transmit optical beams other than the sample beam out of the micro or semiconductor optical bench and optionally making it possible to rely on component placement tolerances for alignment of the reference arm.

FIGS. 2A, 2B, 2E and 2F shows the hybrid solution with external sample and reference arm. Additionally, FIG. 2A shows the use of the ¼ waveplates as part of the hermetic seal at the edge of the micro or semiconductor optical bench.

Hereinafter is provided a description of various hardware and architectures suitable for the present invention.

Optical Coherence Tomography Imaging System

As mentioned above, FIG. 1A shows a generalized optical coherence tomography system suitable for use with the present invention. A variety of ways to create cross-sectional images (e.g., B-scans) are known in the art including but not limited to: along the horizontal or X-direction, along the vertical or Y-direction, along the diagonal of X and Y, or in a circular or spiral pattern. B-scans may be in the X-Z dimensions but may be any cross-sectional image that includes the Z-dimension. An example OCT B-scan image of a normal retina of a human eye is illustrated in FIG. 15. An OCT B-scan of the retinal provides a view of the structure of retinal tissue. For illustration purposes, FIG. 15 identifies various canonical retinal layers and layer boundaries. The identified retinal boundary layers include (from top to bottom): the inner limiting membrane (ILM) Lyer1, the retinal nerve fiber layer (RNFL or NFL) Layr2, the ganglion cell layer (GCL) Layr3, the inner plexiform layer (IPL) Layr4, the inner nuclear layer (INL) Layr5, the outer plexiform layer (OPL) Layr6, the outer nuclear layer (ONL) Layr7, the junction between the outer segments (OS) and inner segments (IS) (indicated by reference character Layr8) of the photoreceptors, the external or outer limiting membrane (ELM or OLM) Layr9, the retinal pigment epithelium (RPE) Layr10, and the Bruch's membrane (BM) Layr11.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2005/0171438, 2012/0307014, 2010/0027857, 2012/0277579 and U.S. Pat. No. 6,549,801, all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en face vasculature image is an image displaying motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

FIG. 1B shows an example of an en face vasculature image. After processing the data to highlight motion contrast using any of the motion contrast techniques known in the art, a range of pixels corresponding to a given tissue depth from the surface of internal limiting membrane (ILM) in retina, may be summed to generate the en face (e.g., frontal view) image of the vasculature. FIG. 1C shows an exemplary B-scan of a vasculature (OCTA) image. As illustrated, structural information may not be well-defined since blood flow may traverse multiple retinal layers making them less defined than in a structural OCT B-scan, as shown in FIG. 15. Nonetheless, OCTA provides a non-invasive technique for imaging the microvasculature of the retina and the choroid, which may be critical to diagnosing and/or monitoring various pathologies. For example, OCTA may be used to identify diabetic retinopathy by identifying microaneurysms, neovascular complexes, and quantifying foveal avascular zone and nonperfused areas. Moreover, OCTA has been shown to be in good agreement with fluorescein angiography (FA), a more traditional, but more invasive, technique requiring the injection of a dye to observe vascular flow in the retina. Additionally, in dry age-related macular degeneration, OCTA has been used to monitor a general decrease in choriocapillaris flow. Similarly, in wet age-related macular degeneration, OCTA can provides a qualitative and quantitative analysis of choroidal neovascular membranes. OCTA has also been used to study vascular occlusions, e.g., evaluation of nonperfused areas and the integrity of superficial and deep plexus.

Computing Device/System

FIG. 1E illustrates an example computer system (or computing device or computer device) in accord with the present invention. In some embodiments, one or more computer systems may provide the functionality described or illustrated herein and/or perform one or more steps of one or more methods described or illustrated herein. The computer system may be integrated into the substrate of a semiconductor optical bench, as discussed above, or may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers, and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above-mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications, and variations as may fall within the spirit and scope of the appended claims.

The invention claimed is:

1. A medical optical tomography system for imaging a sample comprising:

a hermetically sealed micro package housing:

- a base supporting a light source and a beam divider, wherein the light source generates a beam of light, the beam divider directs a first portion of the light into a reference arm and a second portion of the light into a sample arm;
- ii) a transmissive element providing an interface between an inside of the micro package and an outside of the micro package, the transmissive element being along the sample arm and at least partially transparent to the second portion of the light;

a detector configured for receiving light returning from the sample arm and the reference arm, wherein the detector is further configured for generating signals in response to the receiving the light; and a processor configured for converting the signals into image data, wherein the beam divider, the reference arm, and the sample arm are part of a first interferometer;

wherein the base further supports a second interferometer including a second beam splitter, a first mirror and a second mirror, and wherein a fraction of the light from the light source is directed to the second interferometer to generate a clock to linearize a scan sweep of the OCT system.

2. The system of claim 1, wherein:

the optical tomography system is a swept source optical coherence tomography (OCT) system, and the optical tomography system generates an imaging depth large enough so that the sample is always within the optical tomography system depth imaging window;

the detector is housed within the micro package;

the base is a semiconductor substrate and the base includes digitizing circuitry integrated onto the base and the digitizing circuitry is configured to digitize signals from the detector;

the image data being cropped to display, on an electronic display, a desired depth range within the depth imaging window, wherein the desired depth range is changed dynamically during a data acquisition scan to compensate for sample motion.

3. The system of claim 2, wherein the depth range is changed to follow a curvature of the sample.

4. The system of claim 2, wherein the depth range is changed during A-scans within a B-scan.

5. The system of claim 1, wherein:

the optical tomography system generates an imaging depth large enough so that the sample is always within the optical tomography system depth imaging window;

the reference arm is fully enclosed within the micro package and the reference arm has an optical path length mismatch with the optical path length of the sampling arm; and the optical tomography system further comprises an optical modulator supported by the base, and the optical modulator is configured to shift the optical frequency of one of the first portion of the light or the second portion of the light to define a modulated OCT signal with a spectral content corresponding to that obtained if the optical path length of the reference arm more closely matched the imaging depth.

6. A medical optical tomography system for imaging a sample comprising:

a hermetically sealed micro package housing:

i) a base supporting a light source and a beam divider, wherein the light source generates a beam of light, the beam divider directs a first portion of the light into a reference arm and a second portion of the light into a sample arm;

ii) a transmissive element providing an interface between an inside of the micro package and an outside of the micro package, the transmissive element being along the sample arm and at least partially transparent to the second portion of the light;

a detector configured for receiving light returning from the sample arm and the reference arm, wherein the detector is further configured for generating signals in response to the receiving the light; and a processor configured for converting the signals into image data, wherein the optical tomography system generates an imaging depth large enough so that the sample is always within the depth imaging window, wherein the reference arm is fully enclosed within the micro package and the reference arm has an optical path length mismatch with the optical path length of the sampling arm, and wherein the optical tomography system further comprises a frequency mixer supported by the base, and the frequency mixer is configured to frequency-mix the signals from the detector with a frequency corresponding to an edge of the depth imaging window to create a downmixed OCT signal with a spectral content corresponding to that obtained if the optical path length of the reference arm more closely matched the imaging depth.

7. The system of claim 6, wherein the frequency corresponding to an edge of the depth imaging window is determined by use of a preliminary scan sweep at a slow A-scan rate, followed by a faster scan sweep at a faster A-scan rate after determining the frequency corresponding to an edge of the depth imaging window from the preliminary scan sweep.

8. The system of claim 1, wherein the hermetically sealed micro package contains a vacuum.

9. The system of claim 1, wherein the hermetically sealed micro package contains a gas that mitigates degradation of active semiconductor optical materials.

10. The system of claim 1, wherein:

the beam divider is a first polarizing beamsplitter;

the detector that receives the light returning from the sample arm and reference arm is a first detector; and the base further supports:

a first waveplate optically coupling the light source to the first polarizing beamsplitter;

a second waveplate in the sample arm and a third waveplate in the reference arm;

a fourth waveplate and a second polarizing beamsplitter, light returning from the sample arm and reference arm being combined at the first polarizing beamsplitter and sent through the fourth waveplate to the second polarizing beamsplitter that acts as an interference generator; and a second detector, said first detector and second detector being coupled to the second polarizing beamsplitter to generate signals in response thereto.

11. The system of claim 10, wherein the base further supports a pinhole in the optical path between the first polarizing beamsplitter and the second polarizing beamsplitter.

12. The system of claim 10, wherein the second waveplate is the transmissive element.

13. The system of claim 10, wherein the first waveplate, the second waveplate, the third waveplate, and the fourth waveplate all have the same phase delay.

14. The system of claim 10, wherein:

the first waveplate and the fourth waveplate are half-wave plates; and the second waveplate and the third waveplate are quarter-wave plates.

15. The system of claim 1, wherein all sample arm optics are part of the micro package.

16. The system of claim 1, wherein:

the beam divider is a first polarizing beamsplitter;

the detector that receives light returning from the sample and reference arms is supported by the base and is a first detector;

the base further supports:

a first waveplate optically coupling the light source to the first polarizing beamsplitter;

a second waveplate in the sample arm and a third waveplate in the reference arm;

a fourth waveplate and a second polarizing beamsplitter, light returning from the sample and reference arms being combined at the first polarizing beamsplitter and sent through the fourth waveplate to the second polarizing beamsplitter that acts as an interference generator;

a second detector, said first detector and second detector being coupled to the second polarizing beamsplitter to generate signals in response thereto;

a faraday rotator, a fifth waveplate, a sixth waveplate, a third polarizing beamsplitter, a fourth polarizing beamsplitter, a third detector, and a fourth detector;

wherein:

the faraday rotator and second waveplate are in the optical path between the first polarizing beamsplitter and third polarizing beamsplitter;

the third polarizing beamsplitter directs a first portion of the light it receives from the first polarizing beamsplitter to a second reference arm through the fifth waveplate and a second portion of the light it receives from the first polarizing beamsplitter to a second sample arm;

the sixth waveplate optically couples the third polarizing beamsplitter to the fourth polarizing beam splitter;

the third detector and fourth detector receive from the fourth polarizing beamsplitter light returning from the second reference arm and the second sample arm and generate signals in response thereto.

17. The system of claim 1, wherein:

the beam divider is a first polarizing beamsplitter;

the detector that receives light returning from the sample and reference arms is supported by the base and is a first detector;

the base further supports:

a first waveplate optically coupling the light source to the first polarizing beamsplitter;

a second waveplate in the sample arm and a third waveplate in the reference arm;

a fourth waveplate and a non-polarizing beam splitter, light returning from the sample and reference arms being combined at the first polarizing beamsplitter and sent through the fourth waveplate to the non-polarizing beam splitter;

a second polarizing beam splitter and a second detector, the second polarizing beam splitter receiving a portion of the light received by the non-polarizing beam splitter, the first detector and the second detector being coupled to the second polarizing beamsplitter to generate signals in response thereto;

a third polarizing beam splitter, fifth waveplate, a third detector, and a fourth detector, the third polarizing beam splitter receiving though the fifth waveplate a portion of the light received by the non-polarizing beam splitter, the third detector and fourth detector being coupled to the third polarizing beamsplitter to generate signals in response thereto.

18. The system of claim 1, wherein the base further supports a fiber coupler for interfacing the beam divider with the detector.

19. The system of claim 1, wherein the second interferometer is optically coupled to the reference arm of the first interferometer by a partially transmissive mirror.

20. The system of claim 1, wherein:

the light source includes a plurality of lasers each having a different center frequency and a limited wavelength range; and the base further supporting at least one dichroic mirror for combining the light from the plurality of lasers to define a combined sweep bandwidth larger than the individual wavelength range of each laser.

21. The system of claim 1, wherein:

the light source includes a plurality of lasers each having a different center frequency and a limited wavelength range, the plurality of lasers being operated sequentially to sequentially scan the same region on the sample; and the detector sequentially detects the sequential light returning from the sample and reference arms due to the plurality of lasers being operated sequentially.

22. The system of claim 1, wherein the micro package is part of an imaging module, the system further comprising:

a transport system defining a spherical motion;

the imaging module being coupled to the transport system and movable about the spherical motion by the transport system; and a gimbal providing tilt functionality to the imaging module for alignment of the imaging module to a target point on the sample.

23. The system of claim 22, wherein the sample is an eye and the target point is the eye pupil, the system further comprising:

a pupil camera tracking the center of the eye pupil and providing feedback signals to the gimbal to maintain alignment of the imaging module.

24. The system of claim 22, wherein the transport system includes a rotatable struct whose rotation at least partially defines the spherical motion.

25. The system of claim 22, wherein the transport system includes a rotatable spherical surface with a radial guide to move the imaging module radially within the interior of the spherical surface.

26. The system of claim 1, wherein the base is one of a micro optical bench and a semiconductor optical bench.

27. The system of claim 1, wherein the optical tomography system is one of an optical coherence tomography (OCT) system, OCT angiography system, and Optical Coherence Domain Reflectometry (OCDR) system.

28. The system of claim 1, wherein the base has a recessed opening on a surface configured to receive a micro-optic device at a predefined position, elevation, and orientation to achieve a predefined alignment for the micro-optic device.

29. The system of claim 28, wherein the micro package includes a lid coupled to the base, the lid having corresponding opening on a surface facing the surface of the base, the openings on the lid being configured to receive the micro-optic device to maintain the predefined alignment of the micro-optic device.

* * * * *